US009651566B2

(12) United States Patent
Jahnen-Dechent et al.

(10) Patent No.: US 9,651,566 B2
(45) Date of Patent: May 16, 2017

(54) METHOD FOR DETERMINING THE PROPENSITY FOR CALCIFICATION

(71) Applicant: Rheinisch-Westfälische Technische Hochschule Aachen, Aachen (DE)

(72) Inventors: Wilhelm Jahnen-Dechent, Aachen (DE); Andreas Pasch, Bern (CH); Stefan Farese, Solothum (CH); Steffen Gräber, Kerkrade (NL)

(73) Assignee: Rheinisch-Westfällische Technische Hochschule Aachen, Aachen (DE)

( * ) Notice: Subject to any disclaimer, the term of this patent is extended or adjusted under 35 U.S.C. 154(b) by 157 days.

(21) Appl. No.: 14/356,696

(22) PCT Filed: Nov. 7, 2012

(86) PCT No.: PCT/EP2012/071971
§ 371 (c)(1),
(2) Date: May 7, 2014

(87) PCT Pub. No.: WO2013/068372
PCT Pub. Date: May 16, 2013

(65) Prior Publication Data
US 2014/0377874 A1  Dec. 25, 2014

(30) Foreign Application Priority Data
Nov. 7, 2011  (EP) .................................... 11008849

(51) Int. Cl.
*G01N 33/84* (2006.01)
*G01N 21/51* (2006.01)
(Continued)

(52) U.S. Cl.
CPC ............. *G01N 33/84* (2013.01); *G01N 21/51* (2013.01); *G01N 33/48* (2013.01);
(Continued)

(58) Field of Classification Search
CPC .......... G01N 2021/4707; G01N 21/47; G01N 21/49; G01N 21/51; G01N 2800/107;
(Continued)

(56) References Cited

U.S. PATENT DOCUMENTS

| 2003/0027211 A1 | 2/2003 | Price |
| 2005/0186647 A1* | 8/2005 | Gao ................... G01N 33/6893 435/7.93 |
| 2013/0017562 A1* | 1/2013 | Shanahan .......... G01N 33/6893 435/7.92 |

FOREIGN PATENT DOCUMENTS

| JP | H09-072891 | 3/1997 |
| JP | 2002139501 | 5/2002 |

OTHER PUBLICATIONS

Ismail et al. Biosensors and Bioelectronics, vol. 26, May 23, 2011, pp. 4702-4707.*

(Continued)

*Primary Examiner* — Maureen Wallenhorst
(74) *Attorney, Agent, or Firm* — Thorpe North & Western, LLP; David W. Osborne

(57) ABSTRACT

The present invention relates to a method for determining the propensity of a fluid for calcification characterized by the following steps: (i) adding a soluble calcium salt and a soluble phosphate salt to a sample of the fluid; (ii) incubating the sample at conditions allowing the formation of calciprotein particles (CPPs); and (iii) determining one or more of the following: (a) the rate of the formation of primary and/or secondary CPPs; (b) the amount of primary and/or secondary CPPs; and/or (c) the rate of the transition of primary CPPs into secondary CPPs, wherein an increase in one or more of (a), (b) and/or (c) of step (iii) indicates an increased propensity of the fluid for calcification.

19 Claims, 18 Drawing Sheets

(51) Int. Cl.
  *G01N 33/48* (2006.01)
  *G01N 21/47* (2006.01)
(52) U.S. Cl.
  CPC ............... *G01N 2021/4707* (2013.01); *G01N 2800/107* (2013.01); *G01N 2800/323* (2013.01)
(58) Field of Classification Search
  CPC .. G01N 2800/323; G01N 33/48; G01N 33/49; G01N 33/84; G01N 33/20; Y10T 436/16; Y10T 436/166666
  USPC .... 436/34, 43, 63, 73, 74, 79, 86, 103, 105, 436/164; 422/82.05, 82.09, 502, 552; 435/29
  See application file for complete search history.

(56) References Cited

OTHER PUBLICATIONS

Heiss, et al.; Hierarchal Role of Fetuin-A and Acidic Serum Proteins in the Formation and Stabilization of Calcium Phosphate Particles; The Journal of Biological Chemistry; May 23, 2008; pp. 14815-14825; vol. 283, No. 21; The American Society for Biochemistry and Molecular Biology, Inc., United States of America.

Heiss, et al.; Structural Basis of Calcification Inhibition by a 2-HS Glycoprotein/Fetuin-A; The Journal of Biological Chemistry; Apr. 11, 2003; pp. 13333-13341; vol. 278, No. 15; The American Society for Biochemistry and Molecular Biology, Inc., United States of America.

Jahnen-Dechent, et al.; Cloning and Targeted Deletion of the Mouse Fetuin Gene; The Journal of Biological Chemistry; Dec. 12, 1997; pp. 31496-31503; vol. 272, No. 50; The American Society for Biochemistry and Molecular Biology, Inc., United States of America.

Jahnen-Dechent, et al.; Fetuin-A Regulation of Calcified Matrix Metabolism; Circulation Research; Jun. 10, 2011; pp. 1494-1509; vol. 108; The American Heart Association, Dallas, Texas.

Jahnen-Dechent, et al.; Systemic inhibition of spontaneous calcification by the serum protein α 2—HS glycoprotein/fetuin; Z Kardiol; 2001; pp. III/47-III/56; vol. 90, Suppl. 3; Steinkopf Verlag.

Ketteler, et al.; Association of low fetuin-A (AHSG) concentrations in serum with cardiovascular morality in patients on dialysis: a cross-sectional study; The Lancet; Mar. 8, 2003; pp. 827-833; vol. 361, Issue 9360; Elsevier Ltd.

Matsui, et al.; Fully phosphorylated fetuin-A forms a mineral complex in the serum of rats with adenine-induced renal failure; Kidney International; Feb. 4, 2009; pp. 915-928; vol. 75; International Society of Nephrology.

Pasch, et al.; Nanoparticle-Based Test Measures Overall Propensity for Calcifications in Serum; Journal of the American Society of Nephrology; Oct. 2012; pp. 1744-1752; vol. 23, No. 10; The American Society of Nephrology.

Pasch, et al.; Sodium thiosulfate prevents vascular calcifications in uremic rats; Kidney International; Sep. 24, 2008; pp. 1444-1453; vol. 74; International Society of Nephrology.

Reynolds, et al.; Human Vascular Smooth Muscle Cells Undergo Vesicle-Mediated Calcification in Response to Changes in Extracellular Calcium and Phosphate Concentrations: A Potential Mechanism for Accelerated Vascular Calcification in ESRD; Journal of the American Society of Nephrology; 2004; pp. 2857-2867; The American Society of Nephrology.

Reynolds, etal.; Multifunctional Roles for Serum Protein Fetuin-A in Inhibition of Human Vascular Smooth Muscle Cell Calcification; Journal of the American Society of Nephrology; 2005; pp. 2920-2930; The American Society of Nephrology.

Schafer, et al.; The serum protein α 2-Heremans-Schmid glycoprotein/fetuin-A is a systemically acting inhibitor of ectopic calcification; The Journal of Clinical Investigation; Aug. 2003; pp. 357-366; vol. 112, No. 3; American Society for Clinical Investigation.

Wald, et al.; Formation and stability kinetics of calcium phosphate-fetuin-A colloidal particles probed by time-resolved dynamic light scattering; Soft Matter; Jan. 1, 2011; pp. 2869-2874; vol. 7; The Royal Society of Chemistry.

Wu, et al.; Fetuin-A/Albumin-Mineral Complexes Resembling Serum Calcium Granules and Putative Nanobacteria: Demonstration of a Dual Inhibition-Seeding Concepts; PLoS One; Nov. 2009; 40 pages; vol. 4, Issue 11; www.plosone.org.

Young, et al.; Characterization of Granulations of Calcium and Apatite in Serum as Pleomorphic Mineralo-Protein Complexes and as Precursors of Putative Nanobacteria; PLoS One; May 2009; 32 pages; vol. 4, Issue 5; www.plosone.org.

Young, et al.; Putative Nanobacteria Represent Physiological Remnants and Culture By-Products of Normal Calcium Homeostasis; PLoS One; Feb. 2009; 35 pages; vol. 4, Issue 2; www.plosone.org.

Yusuf, et al.; Global Burden of Cardiovascular Diseases: Part I: General Considerations, the Epidemiologic Transition, Risk Factors, and Impact of Urbanization; Circulation; 2001; pp. 2746-2753; vol. 104; The American Heart Association, Dallas, Texas.

PCT Application PCT/EP2012/071971; filed Jul. 11, 2012; Rheinisch-Westfalische Technische Hochschule Aachen; International Search Report mailed Dec. 21, 2012.

PCT Application PCT/EP2012/071971; filed Jul. 11, 2012; Rheinisch-Westfalische Technische Hochschule Aachen; International Preliminary Report on Patentability issued May 13, 2014.

\* cited by examiner

METHOD FOR DETERMINING THE PROPENSITY FOR CALCIFICATION

The present invention relates to a method for determining the propensity of a fluid for calcification.

In nature, the deposition of calcium salts is an abundant phenomenon found in living and non-living environments, in vivo and in vitro. It may occur whenever fluids comprising calcium salts get in contact with surfaces or may even occur in solution. A high degree of calcification may harm technical devices in vitro and may harm patients when it occurs in vivo, in particular in the cardiovascular system and in soft tissues.

Today, cardiovascular and soft tissue calcifications are a major health problem and one of the leading causes of death worldwide. Calcification is a widespread and highly important process characterized by the deposition of calcium salts that may occur throughout the whole body. Typical examples for the precipitation of calcium salts are the precipitation of calcium phosphates, calcium carbonates and complexes thereof.

Interestingly, in vivo, calcium and phosphate concentrations are typically supersaturated in most tissues and body fluids throughout the body, thereby creating a continuous chemical pressure towards calcification. Under physiological conditions however, calcium and phosphate only precipitate in bones and teeth, whereas soft tissues in a healthy patient do not or merely slightly and slowly calcify. This indicates that, in vivo, the precipitation of calcium is a well-regulated and site-specific process.

However, calcification may also occur in other tissues and organs and may, hereby, be pathological. For instance, calcification may cause soft tissues such as the skin, brown fat, lung, kidney, heart or a joint to harden. Here, calcification may lead to a pathological tissue and potentially to a corresponding pathological condition including the clinical symptoms thereof. Moreover, calcification may occur in the lumen of certain organs such as the kidney, in particular the renal pelvis, the ureter, the bladder, the gallbladder and the bile duct. Here, a kidney stone (nephrolith) and a gallstone, respectively, may occur.

Nevertheless, the most common pathological calcification is atherosclerosis. Mild forms of atherosclerosis mostly occur in elderly people without provoking any clinical symptoms. However, cardiovascular calcification may increase the risk of numerous diseases such as, e.g., hypertonia, myocardial infarction, limb ischemia and cerebral apoplexy (stroke). These cardiovascular diseases have become the leading cause of death and a major challenge for healthcare Systems worldwide (Yusuf et al., 2001). Highly pronounced forms of calcification may further lead to the necessity of amputation of an extremity such as, e.g., a leg, an arm, a foot or a hand. The process of in vivo cardiovascular and soft tissue calcification is not fully understood so far. It is considered that several chemical factors may play an important role in calcification. Such chemical factors may be inter alia vitamin D, oxalic acid, cortisol and calcium-binding polypeptides.

Cardiovascular and soft tissue calcification may be regarded as the result of actively regulated cellular processes leading to a transformation of vascular smooth muscle cells into osteoblast-like cells (Reynolds et al, 2004; Reynolds et al, 2005). These cells are considered to process and handle surplus amounts of calcium and phosphate and deposit these extracellularly in the form of crystalline hydroxyapatite ($Ca_{10}(PO_4)_6(OH)_2$) which is also the main component of the inorganic bone substance.

As an additional conceptual view on pathologic biomineralization, it is considered that the process of calcification also may be of a passive and unregulated nature and that it takes place preferentially in situations characterized by an unfavorable interplay of serum-bound factors of calcification (Jahnen-Dechent et al, 2001; Schäfer et al., 2003; Heiss et al., 2008). Blood serum components may jointly undertake the task of preventing the supersaturated calcium and phosphate concentrations from precipitating. Calcium may be bound in calcium-comprising particles (Wald et al., 2011; Heiss et al., 2003), which may spontaneously convert into secondary calcium-comprising particles in a transitional ripening step associated with an increase in particle diameter (Wald et al., 2011). Herein, fetuin-A is known to serve as a regulator of calcified matrix metabolism (Jahnen-Dechent et al., 2011).

Due to the severe consequences that calcification may have, it is of considerable importance to have a reliable method for determining the overall propensity of a body fluid for calcification, taking into account all known and unknown factors inhibiting and promoting calcification in the fluid. This is of particular importance for diagnosing the risk of calcification in a patient who has developed calcified plaques or is at risk of developing calcified plaques. The risk of calcification is especially high in patients with reduced or absent function of the kidney, the major organ of mineral metabolism. Thus dialysis patients have an exceptionally high risk of vascular and valvular calcification with highly increased morbidity and mortality.

In the state of the art, the propensity for calcification in an individual who is potentially at risk of developing calcified plaques is assessed by determining the phosphate concentration or the calcium phosphate product in the serum of the patient. If this concentration exceeds a certain threshold, phosphate binders are administered in order to decrease the phosphate uptake and thereby to prevent calcium precipitation.

However, the phosphate concentration in the serum does not necessarily correlate with the propensity for calcification. In fact, there are individuals bearing a normal phosphate concentration in the serum but, nevertheless, have a severely increased risk of developing calcified plaques or even have developed calcified plaques already. On the other hand, there are also individuals who bear an increased phosphate concentration in the serum, but who never develop any calcified plaques.

In the view of the above, the methods for determining the propensity of a fluid for calcification known in the art are not reliable as they do not provide any information of the overall propensity of said fluid for calcification.

Therefore, today, there is still an unmet need for reliable methods for determining the overall propensity of a fluid for calcification. This is of particular importance for diagnosing the risk of calcification in a patient who has developed calcified plaques or is at risk of developing calcified plaques.

Surprisingly, we found that the overall propensity of a fluid for calcification can be determined by a method based on determining the rate of the formation of primary and/or secondary CPPs, the amount of primary and/or secondary CPPs and/or the rate of the transition of primary CPPs into secondary CPPs.

The present invention relates to a method for determining the propensity of a fluid for calcification, wherein said method is characterized by the following steps:

(i) adding a soluble calcium salt and a soluble phosphate salt to a sample of said fluid;
(ii) incubating said sample at conditions allowing the formation of calciprotein particles (CPPs); and
(iii) determining one or more of the following:
  (a) the rate of the formation of primary and/or secondary CPPs;
  (b) the amount of primary and/or secondary CPPs; and/or
  (c) the rate of the transition of primary CPPs into secondary CPPs,
wherein an increase in one or more of (a), (b) and/or (c) of step (iii) indicates an increased propensity of said fluid for calcification.

As used herein, the term "calcification" may be understood in the broadest sense as any deposition and/or precipitation of poorly soluble or insoluble calcium salts and/or the formation of calciprotein particles (CPPs) in vivo and in vitro. As used herein, the terms "calcification", "calcinations", "calcium deposition" and "calcium precipitation" may be understood interchangeably. Optionally, calcification may lead to the formation of calcified plaque(s), may be microcalcification and/or may be the precipitation of calcium salts in solution, thus, the formation of insoluble or poorly soluble calcium-comprising particles, including but not limited to primary and/or secondary CPPs.

As used in the context of the present invention, the term "poorly soluble" may be understood in the sense that the salt may bear a solubility of less than 10 mM, less than 1 mM, less than 0.1 mM, less than 10 µM, less than 1 µM, less than 0.1 µM or less than 10 nM in water at 20° C. The term "insoluble" may be understood in the sense that the salt may bear a solubility of less than 10 nM, less than 1 nM or less than 0.1 nM in water at 20° C.

Preferably, calcification is calcification in vivo. This means that the calcification occurs in the fluid when the fluid is within a body of a subject and the propensity for said in vivo calcification is determined by the present method. The fact that calcification may be calcification in vivo may not exclude that the method may also be performed in vitro. As used throughout the invention, the terms "perform" and "conduct" may be understood interchangeably. Preferably, the method itself is performed in vitro, thus, is not practiced on the human or animal body. However, the results obtained by the method are usable for diagnosis of the patient.

In the context of calcification in vivo, calcification may also be understood as the formation of one or more calcified plaque(s). In this context, the terms "calcified plaque" and "calcified lesion" may be understood interchangeably. Plaque formation may occur in various areas of the patient's body. More preferably, calcification is vascular calcification, valvular calcification, cardiovascular calcification or calcification of one or more soft tissue(s). Most preferably, calcification is cardiovascular calcification.

Cardiovascular calcification as used herein may be understood in the broadest sense as the formation of one or more plaque(s) localized in one or more blood vessel(s), more preferably at the tunica intima and/or the tunica media. Plaque formation in a blood vessel may also be designated as the formation of intravascular plaque. This intravascular plaque may be one reason for the calcification of blood vessels in the body of the patient designated as "cardiovascular calcification". Cardiovascular calcification, thus, the formation of calcified lesions in the cardiovascular system, may increase the risk of numerous diseases such as hypertonia, myocardial infarction and cerebral apoplexy (stroke). Highly pronounced forms of calcification may further lead to the necessity of amputation of an extremity such as a leg.

One severe form of pathological cardiovascular calcification is "Mönckeberg's atherosclerosis", also called "medial calcific sclerosis". Here, the vessels harden as calcium deposits form in the middle layer of the walls of medium sized vessels (tunica media). Consequently, the pulse pressure is pathologically increased. Plaque formation may be characterized by fatty streaks. These fatty streaks are typically characterized by an accumulation of fatty acids, cholesterol and/or one or more other steroid(s). Often, these plaque formations (plaques) are further characterized by the incorporation of low-density lipoprotein (LDL) and/or white blood cells, especially macrophages that have taken up oxidized low-density lipoprotein (LDL). After these white blood cells have accumulated large amounts of cytoplasmic membranes they are also designated as foam cells. In a later stage of plaque formation, an extracellular lipid core may be formed. Further, the outer and/or older portions of the plaque may become more calcific, less metabolically active and more physically stiff over time. The plaque may further comprise various amounts of cellular debris, calcium and/or fibrous connective tissue. Optionally it may form a fibrous cap. Finally, plaque may potentially lead to platelet clotting, atherosclerosis and/or stenosis.

In the context of the present invention, calcification in vivo may also be understood as calcification in the lumen of certain organs such as the kidney, in particular in the renal pelvis, the ureter, the bladder, the gallbladder and/or the bile duct. As a result, a kidney stone (nephrolith) and a gallstone, respectively, may occur. Kidney stones and gallstones frequently occur throughout the population and may lead to severe symptoms. Moreover, calcification may occur in soft tissues and may cause soft tissues to harden. Here; calcification may lead to a pathological tissue and potentially to a corresponding pathological condition including potentially severe clinical symptoms. Several types of tumours such as certain types of brain tumours bear a distinctive local calcification (calcium spots), though calcium spots of different sizes may also occur in the brain without provoking any clinical symptoms or indicating any pathological condition.

As used in the context of the present invention, calcification may also be calcification associated with any deposit mainly composed of one or more organic material(s). Exemplarily, this deposit may be, e.g., a kidney stone, a gallstone, plaque formation and/or a precursor of one thereof. Preferably, these deposits may be plaque formation.

Alternatively, calcification is calcification in vitro. As used herein, the terms "in vitro" and "ex vivo" may be understood interchangeably. Calcification in vitro may occur in any environment outside the body. Exemplarily, calcification in vitro in the context of the present invention may occur in any hollow device getting in contact with a fluid, preferably an aqueous fluid. In a medicinal context, said hollow device may exemplarily be a needle, an acus, a tube, a syringe, a dialysis machine, a dialysis membrane, or a blood or plasma preservation. Alternatively, said hollow device may also be a tube, a pipe (e.g., a water pipe), a washing machine, a dishwasher, a water boiler, a kettle, a pot a pan, a coffee machine, a tea machine, a washing basin, a bath tub, a toilette, an urinal or any machine or part of a machine getting in contact with a calcifying fluid.

As used in the context of the present invention, the term "fluid" may be understood in the broadest sense as any fluid that may lead to calcification. As used herein, the terms "fluid", "liquid" and "solution" may be understood interchangeable. Preferably, the fluid is an aqueous fluid, thus, a fluid comprising more than 50% (w/w) water, more than 60% (w/w) water, more than 70% (w/w) water, more than 80% (w/w) water, more than 90% (w/w) water, or more than 95% (w/w) water. The fluid may be a body fluid or may be a technical fluid.

As used in the context of the present invention, the term "propensity of a fluid for calcification" may be understood in the broadest sense as the tendency of a fluid to bear calcification. The propensity for calcification may also be understood in the broadest sense as the calcification pressure and, therefore, the potency of a fluid to bear calcification. Therefore, in case the propensity of a fluid for calcification is high, the fluid will likely show calcification upon increasing the calcium and/or phosphate concentration, whereas in case the propensity of a fluid for calcification is low, the fluid will likely not show calcification or show very little calcification upon increasing the calcium and/or phosphate concentration. In the context of the present invention, the propensity of a fluid for calcification is preferably the overall propensity of a fluid for calcification, thus, the propensity for calcification mediated by the fluid as a whole in a macroscopic view.

The propensity of a fluid for calcification is the opposite of the propensity of a fluid to prevent calcification. Consequently, the present invention also refers to a method for determining the propensity of a fluid for the prevention of calcification. In this context, the prevention or inhibition of calcification may also be designated as "humoral line of defense". This humoral line of defense may be overwhelmed by increased calcium and/or phosphate concentrations.

As used herein the term "determining" may be understood in the broadest sense as the characterization of the state and strength of the propensity of a fluid for calcification. In this context, the term "determining" may optionally include but may not be limited to any one of the steps of examining, testing, measuring, investigating, assaying, exploring and assessing the propensity of a fluid for calcification. In the context of determining the propensity of a fluid for calcification in a sample obtained from a patient, said determining may be also be understood interchangeably with the term "diagnosing".

As used in the context of the present invention, the term "sample of said fluid" may be understood in the broadest sense as any composition comprising the fluid. In the context of the present invention, the terms "sample of said fluid", "sample of the fluid" and "sample" may be understood interchangeably. Preferably, the sample is a fluid sample. As used herein, the terms "liquid" and "fluid" may be understood interchangeably. Most preferably, the sample is an aqueous sample. The sample may comprise less than 5% (v/v), more than 5% (v/v), more than 10% (v/v), more than 20% (v/v), more than 30% (v/v), more than 40% (v/v), more than 50% (v/v), more than 60% (v/v), more than 70% (v/v), more than 80% (v/v), more than 90% (v/v) of the fluid or may even be composed of fluid only. Preferably, the sample may comprise between 25% (v/v) and 75% (v/v) fluid, most preferably comprise between 30% (v/v) and 60% (v/v) fluid. However, the person skilled in the art will notice that the amount of fluid in the sample will depend on the type of fluid, the applied read out method as well as the calcium and phosphate concentration in the sample.

The term "adding a soluble calcium salt and a soluble phosphate salt" may be understood in the broadest sense as the addition of calcium and phosphate ions to the sample.

As used herein, the term "soluble calcium salt" refers to any salt comprising calcium cations ($Ca^{2+}$) that is soluble in water.

As throughout the present invention, the term "soluble salt" may be understood in the broadest sense as a salt having a solubility of more than 10 nM, more than 0.1 µM, more than 1 µM, more than 10 µM, more than 0.1 mM, more than 1 mM or more than 10 mM in water at 20° C.

As used herein, the term "soluble calcium salt" refers to any soluble salt comprising calcium cations ($Ca^{2+}$). Exemplarily, the soluble calcium may be calcium chloride ($CaCl_2$). The person skilled in the art will understand that the applied concentration of calcium cations will depend on the amount of fluid in the sample, the type of the fluid, the applied read out method as well as the phosphate concentration in the sample. Preferably, calcium ions are added to the sample as an aqueous solution in water or in an appropriate buffer, wherein soluble calcium salt is soluble, such as, e.g., in Hepes buffer at extensively neutral pH. Alternatively, a calcium salt may also be dissolved directly in the sample of the fluid.

As used herein, the term "soluble phosphate salt" refers to any soluble salt comprising at least one of phosphate ($PO_4^{3-}$), hydrogenphosphate ($HPO_4^{2-}$) and/or dihydrogen phosphate ($H_2PO_4^-$) cations. Exemplarily, the soluble phosphate salt may be sodium hydrogen phosphate ($Na_2HPO_4$) and/or sodium dihydrogen phosphate ($NaH_2PO_4$). Preferably, the soluble phosphate salt is added to the sample as an aqueous solution in water or in an appropriate buffer, wherein also calcium cations are soluble, such as, e.g., in Hepes buffer at extensively neutral pH. Alternatively, the soluble phosphate salt(s) may also be dissolved directly in the sample of the fluid.

In fact, the used concentrations of soluble calcium and phosphate salts are chosen in a range were differences are well observable between different samples. Therefore, the overall concentrations of calcium and phosphate, i.e., the concentrations of intrinsic and added calcium and phosphate in sum, may preferably exceed the solubility product of calcium phosphate in water or buffer. On the other hand, said overall concentrations of calcium and phosphate should preferably not exceed the maximal capacity of the precipitation-inhibiting properties of the fluid contained in the sample by more than five orders of magnitude, more than four orders of magnitude, more than three orders of magnitude, more than two orders of magnitude or more than one order of magnitude. Preferably calcium and phosphate are added to the sample independently in order to avoid the formation of calcium phosphate precipitates in a solution before getting in contact with the sample.

Preferably, the concentrations of calcium and phosphate may be supersaturated in the sample. Thus, the product of calcium× phosphate is supersaturated in the sample.

Beside the fluid and the soluble calcium and phosphate salts, the sample may further comprise any other inorganic and/or organic components which do not disturb the method. The sample may further comprise a buffer which does not disturb the method such as, e.g., Hepes buffer. The pH may be adjusted at any pH. Preferably, the pH may be at an extensively neutral pH, i.e., between pH 5.5 and pH 8.0, more preferably between pH 6.0 and pH 8.0, even more preferably between pH 6.5 and pH 7.8, even more preferably between pH 7.2 and pH 7.6, most preferably at a physiological pH, i.e. at a pH at approximately pH 7.4.

The sample may be admixed manually or automatically. The sample volume may depend on the applied detection method and will typically vary between the nanoliter range for small microarray setups up to the milliliter range for macroscopic arrays such as, e.g., centrifugation- or column-based methods.

The samples will typically be used directly obtained from their source (e.g., from a patient or from a technical device) or within few minutes or few days. When the samples are stored for more than few hours, the samples may preferably be stored at room temperature or in the fridge. Alternatively, the samples may also be stored in a frozen, deep-frozen or freeze dried state and may then be stored at any temperature below the freezing point, such as, e.g., at −20°, −80° C. or in liquid nitrogen. A freeze-dried powder may also be stored at ambient temperature.

As used herein, the term "incubating" may be understood in the broadest sense as subjecting the sample of the fluid to conditions allowing the formation of CPPs.

As used herein, the term "conditions allowing the formation of CPPs" refers to any conditions in which CPPs may be formed. Typically said CPPs may comprise poorly soluble calcium phosphate.

Preferably, the sample may be incubated at an extensively neutral pH, i.e., at conditions between pH 5.5 and pH 8.0, more preferably between pH 6.0 and pH 8.0, even more preferably between pH 6.5 and pH 7.8, even more preferably between pH 7.2 and pH 7.6, most preferably at a physiological pH, i.e. at a pH at approximately pH 7.4.

As a precipitation reaction will typically be temperature-sensitive, for comparison of different samples with another and/or for comparison with a calibrating curve, the temperature or temperature profile is set to be in a comparable range. Most preferably, the sample is incubated at a constant temperature and the difference in temperature between samples to be compared with another should be less than 5° C., less than 4° C., less than 3° C., less than 2° C., less than 1° C., less than 0.5° C., less than 0.25° C. or even less than 0.1° C. Preferably, the constant temperature may be in the range of from 0° C. to 100° C., more preferably in the range of from 0° C. to 45° C., even more preferably in the range of from 4° C. to 42° C., even more preferably in the range of from 20° C. to 40° C., even more preferably in the range of from 36° C. to 38° C., even more preferably in the range of from 36.0° C. to 37.5° C. and most preferably in the range of from 36.5° C. to 37.0° C.

Alternatively, the temperature may be varied during the measurement in the form of a temperature profile. This temperature profile may also be comparable in all samples to be compared with another.

As use in the context of the present invention, the terms "calciprotein particle", "calcium protein particle", "calcified protein particle" and "CPP" may be understood in the broadest sense as any particle comprising calcium cations. The terms "protein", "polypeptide" and "peptide" may be understood interchangeably throughout the invention. In the context of the present invention, the terms "particle", "nanosphere", "precipitate", "colloid" and "aggregate" may be understood interchangeably. In the context of the formation of CPPs, the particles are preferably formed by the accumulation of molecules in a sample solution. Preferably, in the CPPs, the calcium cations form a poorly soluble salt. Exemplarily said poorly soluble salt may be calcium phosphate and/or one or more complex(es) thereof. Optionally, said poorly soluble salt may form crystals, preferably crystals in the nanometer or micrometer range, most preferably in the nanometer range. The regular crystal structure may optionally interrupted by the incorporation of one or more polypeptide(s) or other molecules. However, the CPP may further comprise any other inorganic or organic molecule(s) and/or ion(s) found in the fluid and/or added to the sample such as, e.g., one or more polypeptide(s) that may interact with calcium (e.g., a fetuin polypeptide (e.g., fetuin-A), an albumin polypeptide (e.g., serum albumin), calbindin, S-100 protein(s), osteocalcin, vitamin D dependent calcium binding protein, lactoferrin, lactoferricin), organic anions (e.g. oxalate), inorganic anions (e.g., carbonate and/or pyrophosphate), organic cations, inorganic cations (e.g., magnesium and/or $H^+$ ions), vitamins (e.g., vitamin D), hormones (e.g., steroids, thyroxin). It will be understood by a person skilled in the art that a CPP may in general preferably comprise components interacting with calcium anions and/or calcium salts and other components interacting with said components interacting with calcium anions and/or calcium salts. However, other molecules, in particular hydrophobic molecules, may also accumulate in a precipitate.

In the context of the present invention, a CPP is preferably a solid or semi-solid particle. Therefore, the formation of CPPs in a fluid sample leads to a suspension. A CPP may have any size. Preferably, a CPP has a size in the nanometer or micrometer range. As used in this context, the term "size" means the average diameter of the precipitates.

Optionally, the CPPs may further be fluorescently stained, such as e.g., by admixing a fluorescent polypeptide (e.g., cyan fluorescent protein (CFP), green fluorescent protein (GFP) or yellow fluorescent protein (YFP), red fluorescent protein (RFP), mCherry, etc.), a small-molecule dye (e.g., a Cy dye (e.g., Cy3, Cy5, Cy5.5, Cy 7), an Alexa dye (e.g., Alexa Fluor 488, Alexa Fluor 546, Alexa Fluor 647, Alexa Fluor 680, Alexa Fluor 750), a Visen dye (e.g. VivoTag680, VivoTag750), an S dye (e.g., S0387), a DyLight fluorophore (e.g., DyLight 750, DyLight 800), an IRDye (e.g., IRDye 680, IRDye 800), a fluorescein dye (e.g., fluorescein, carboxyfluorescein, fluorescein isothiocyanate (FITC)), a rhodamine dye (e.g., rhodamine, tetramethylrhodamine (TAMRA)) or a HOECHST dye), a quantum dot or a combination of two or more thereof. However, preferably, the CPPs are not fluorescently stained.

Depending on its components, a CPP of the present invention may be an extensively spherical particle, a spindle shape particle, a particle of random shape or a crystalline particle. Primary CPPs are extensively spherical (cf. FIG. 5A), whereas a secondary CPPs bear a spindle or random shape (cf. FIG. 5B). Depending on the used method, the different shape may or may not have influence on the light scattering properties of the particle. Preferably, it has influence on light scattering.

In the context of CPPs, the person skilled in the art will discriminate between primary and secondary CPPs (cf. Jahnen-Dechent et al., 2011). The primary CPPs have a smaller diameter than the secondary CPPs. Further, the primary CPPs bear an extensively spherical shape, whereas the secondary CPPs bear a rather random shape.

In this context, the terms "primary calciprotein particles" and "primary CPPs" may be understood in the broadest sense as particles that are initially be formed within a short time of few seconds or few minutes after adding the soluble calcium salt and the soluble phosphate salt to the sample of the fluid. The average diameter of the primary CPPs is below 100 nm. Preferably, the size of primary CPPs will be in the range of between 50 nm and 100 nm, most typically in the range of about 60 nm to 75 nm. However, it will be understood by a person skilled in the art that the size will also depend on the specific concentrations and conditions used in the method. Typically, as protein components, primary CPPs mainly comprise fetuin-A and albumin.

In this context, the terms "secondary calciprotein particles" and "secondary CPPs" may be understood in the broadest sense as particles that are formed upon incubation by the spontaneous transition of primary CPPs in a transitional ripening step. This step may also take place in a timed and coordinated manner. Typically, this transition will also be associated with an increase in particle diameter (Wald et al., 2011). This transition step may require considerably more time than the initial formation of the primary CPPs. The person skilled in the art will notice that the transition rate depends on the reaction conditions. Typically, the extensive completeness of the transition step may require time in the range of several minutes, several hours, several days, several weeks or even several months. The extensive completeness of the transition step may require more than 1 min, more than 5 min, more than 10 min, more than 30 min, more than 1 h, more than 2 h, more than 6 h, more than 12 h, more than one day, more than two days, more than one week, more than one month, more than six months or even more than one year. The average diameter of the secondary CPPs is larger than 100 nm. Typically, the secondary CPPs may have a size in the range of between 100 nm and 500 nm, most typically in the range of about 100 nm to 200 nm. However, it will be understood by a person skilled in the art that the size will also depend on the specific concentrations and conditions used in the method. Typically, as protein components, secondary CPPs comprise fetuin-A, albumin and further high and low molecular weight components. Preferably, these further protein components have a molecular mass of between 5 and 150 kDa, more preferably of between 10 and 100 kDa. Further, high-molecular weight complexes may occur having a molecular mass of larger than 150 kDa.

As used in the context of the present invention, the term "rate of the formation of primary CPPs" may be understood in the broadest sense as the rate of the generation of primary CPPs in a fluid over time. This may be exemplarily quantified as the amount of primary CPPs, as the volume of primary CPPs or as the mass of primary CPPs in a specific fluid or sample volume. Typically, the primary CPPs will be formed initially in the fluid or sample and may disappear or diminish in amount upon by the transition of primary CPPs into secondary CPPs. The formation of primary CPPs will typically depend on the calcium, the phosphate, the magnesium and the proton concentration of the fluid as well as the concentration of calcification inhibitors and promoters.

As used in the context of the present invention, the term "rate of the formation of secondary CPPs" may be understood in the broadest sense as the rate of the generation of secondary CPPs in a fluid over time. This may be exemplarily quantified as the amount of secondary CPPs, as the volume of secondary CPPs or as the mass of secondary CPPs in a specific fluid or sample volume. Typically, the secondary CPPs will be formed by the transition of primary CPPs into secondary CPPs. Like the formation of primary CPPs, also the formation of secondary CPPs will typically depend on the calcium, the phosphate, the magnesium and the proton concentration of the fluid as well as the concentration of calcification inhibitors and promoters.

As used in the context of the present invention, the term "determining the rate of the formation" may be understood in the broadest sense as the observance and quantification of alterations in the generation of CPPs. As indicated above the formation of CPPs may typically lead to an increased turbidity of the solution. The absorption of the solution and the light scattering properties of the solution increase. The formation rate may be determined by any means known in the art. Exemplarily, it may be determined my means of any method known in the art.

As used in the context of the present invention, the term "amount of primary and/or secondary CPPs" refers to the number of primary and/or secondary CPPs comprised in a specific volume of the fluid or the sample, the mass of the primary and/or secondary CPPs comprised in a specific volume of the fluid or the sample or the volume of the primary and/or secondary CPPs comprised in a specific volume of the fluid or the sample. The mass of primary and/or secondary CPPs comprised in a specific volume may be determined as the mass of the dry particles or the mass of the particles in solution.

As used in the context of the transition of primary CPPs into secondary CPPs, the term "transition" may be understood in the broadest sense as the rearrangement of the calcium-comprising particles, i.e., the calciprotein particles (CPPs), upon incubation, namely, the conversion of one type of CPPs, i.e., primary CPPs, into another type of CPPs, i.e., secondary CPPs. Herein, the terms "transition", "conversion" and "rearrangement" may be understood interchangeably. The transition may also be understood as a transitional ripening step. This step may takes place in a timed and coordinated manner. Typically, the transition will be associated with an increase in particle diameter.

As used in the context of the present invention, the term "transition rate" may be understood in the broadest sense as the kinetic of the transition of primary CPPs into CPPs. Typically, the transition rate is quantified as the time point of the half maximal transition time ($T_{50}$) of the transition of primary CPPs into secondary CPPs. In the context of the present invention, it is demonstrated that the transition rate preferably is delayed in the presence of magnesium ($Mg^{2+}$) and accelerated in the presence of phosphate ($PO_4^{3-}$, $HPO_4^{2-}$, $H_2PO_4^-$) (cf., FIG. 2A).

As used in the context of the present invention, the term "determining the transition rate" may be understood in the broadest sense as the observance and quantification of alterations in the average size of CPPs. As mentioned above, in the context of the present invention, transition will typically mean an increase in size of the CPPs. The transition rate may be determined by any means known in the art. Exemplarily, it may be determined my means of an optical method (e.g., measuring the absorption, detecting changes in light scattering, detecting changes in laser diffraction and/or correlation spectroscopy).

As used in the context of the present invention, the term "increased formation rate" may be understood in the broadest sense as the occurrence of a faster formation of primary and/or secondary CPPs.

As used in the context of the present invention, the term "increased amount" may be understood in the broadest sense as the occurrence of a higher number, amount or volume of primary and/or secondary CPPs.

As used in the context of the present invention, the term "increased transition rate" may be understood in the broadest sense as the occurrence of a faster transition of primary CPPs into secondary CPPs. In this context, the transition rate $T_{50}$ determined for a sample of the fluid may be compared with a one or more control sample(s).

As used herein, the term "increased propensity for calcification" may be understood in the broadest sense as the occurrence of a higher propensity of a fluid for calcification. Therefore, a fluid with increased propensity for calcification will have a higher tendency to precipitate insoluble or poorly soluble calcium salt(s). Thus, increased propensity for calcification also means that the likelihood of the occurrence of calcification and/or the intensity of calcification is increased.

Preferably, step (iii) of the method of the present invention at least comprises determining the transition rate of the transition of primary CPPs into secondary CPPs (step (c)).

In a preferred embodiment, the step of determining one or more of the rate of the formation of primary and/or secondary CPPs, the amount of primary and/or secondary CPPs and/or the rate of the transition of primary CPPs into secondary CPPs (step (iii)) is performed by an optical method, in particular an optical method selected from the group consisting of:
absorptiometry,
detection of light scattering,
correlation spectroscopy,
or a combination of two or more thereof.

As used in the context of the present invention, the term "optical method" may be understood in the broadest sense as any method wherein light is used for the detection, characterization and/or quantification of primary and secondary CPPs. The optical method may be a visual method such as e.g., a microscopic method, or may be a non-visual method such as, e.g., the detection of light scattering or laser diffraction or correlation spectroscopy.

As used in the context of the present invention, the term "absorptiometry" may be understood in the broadest sense as the determination of the absorption or extinction of the fluid of the present invention. Typically, the absorption of the solution will increase upon the formation of primary and secondary CPPs as the turbidity increases. This turbidity may be assessed by the naked eye bay comparison with one or more calibration sample(s) or may be measured by a technical device. Also the transformation of primary CPPs into secondary CPPs may have an influence on the absorption. Absorptiometry may be performed by any device known in the art such as, e.g., a photometer using a cuvette or a plate reader using a microtiter plate (e.g., a 96-well plate or a 386-well plate). Absorptiometry may be performed using light of any wavelength suitable in the art. Preferably, the wavelength will be in the range of between 100 nm and 2000 nm, more preferably in the range of between 200 nm and 1500 nm, even more preferably in the range of between 250 nm and 1000 nm, more preferably in the range of between 280 nm and 1000 nm, more preferably in the range of between 300 nm and 900 nm, more preferably in the range of between 400 nm and 800 nm. The person skilled in the art will recognize that the chosen wavelength is preferably in the range where neither the cuvette or microtiter plate, nor the sample fluid itself shown a considerable absorption.

As used throughout the invention, the wavelength of the excitation light may be chosen by the choice of a particular light source (e.g., a laser bearing specific laser lines), by conduction of the excitation light through one or more filter(s), one or more semipermeable mirror(s) and/or one or more acusto-optical beam splitter(s) and/or by splitting the light into particular wavelength(s) by means of one or more prism(s) and/or one or more optical grid(s). Likewise, the light passed the sample may be conducted through one or more filter(s), one or more semipermeable mirror(s) and/or one or more acusto-optical beam splitter(s) and/or by splitting the light into particular wavelength(s) by means of one or more prism(s) and/or one or more optical grid(s) in order to enable the detection of one or more specific wavelength(s).

Light may be detected by any device known in the art. Exemplarily, the detector(s) may be avalanche photo diode(s) (APD(s)), a photomultiplier tune(s) (PMT(s)) and/or a diode array. A diode array may comprise more than four, more than ten, more than 100, more than 1000 or even more than 10000 diodes.

As used in the context of the present invention, the term "light scattering" may be understood in the broadest sense as any form of scattering in which light is the form of propagating energy which is scattered. Light scattering is a phenomenon well-known by those skilled in the art. Therefore, light scattering may be the deflection of a ray from a straight path. Exemplarily, it may be provoked by irregularities in the propagation medium. In the context of the present invention, said irregularities in the propagation medium are preferably caused by the CPPs in the sample and the interface between the sample fluid and said CPPs. The scattering detected in the context of the present invention is mainly a diffuse scattering due to the random and dense distribution of the CPPs throughout the sample. The shape of the particles may have influence on the light scattering properties of the particles. The light scattering may further depend on the wavelength of the light being scattered, therefore, on the frequency of the excited light. As used herein, the terms "excited light" and "incident light" may be understood interchangeably.

As used in the context of the present invention, the term "detection of light scattering" may be understood in the broadest sense as any method known in the art for the identification, determination and quantification of scattered light. Typically, a light beam of a light of any light source is excited into the sample and the light scattered in one, two or more angle(s) to the irradiating light beam is detected.

Detection of light scattering may be performed by any method known in the art. Exemplarily, detection of light scattering may be detection of Rayleigh scattering, Raman scattering, Mie scattering, Tyndall scattering, Brillouin scattering. Preferably, light scattering is mainly Rayleigh scattering.

In the context of the present invention, Rayleigh scattering is the elastic scattering of light by the particles of the CPPs, wherein the wavelength of the scattered light typically is smaller than the wavelength of the excited light. The intensity of Rayleigh scattering is dependent on the size of the particles. Typically, it is extensively proportional the sixth power of their diameter and extensively inversely proportional to the fourth power of the wavelength of the excited light. The wavelength of the used excitation light will typically be at a comparably short wavelength below 400 nm, below 350, below 300 nm, below 250 nm, below 200 nm or even below 150 nm. However, a person skilled in the art will notice that regarding to the experimental setup also other wavelengths may be applicable.

Raman scattering is well-known by those skilled in the art and bases on inelastic light scattering, wherein the light interacts with optical phonons, which are predominantly intra-molecular vibrations and rotations. Standard spectrometers using scanning monochromators may be used to measure Raman scattering. Mie scattering is a broad class of scattering of light by spherical particles, in particular spherical particles much larger than the wavelength of the excited light. The scattering intensity is generally not strongly dependent on the wavelength, but is sensitive to the particle size. Mie scattering intensity for large particles is extensively proportional to the square of the particle diameter. Tyndall scattering is similar to Mie scattering without the restriction to spherical geometry of the particles. It is particularly applicable to the colloidal suspensions of the present invention. Brillouin scattering occurs from the interaction of photons with acoustic phonons in solids, which are vibrational quanta of lattice vibrations, or with elastic waves in liquids.

More preferably, the sample is excited by a laser beam and detection of the scattered light is measured in one, two or more angle(s). Most preferably, light scattering is detected by nephelometry.

The forward scattered light (measured at an angle of between 160° and 180°) and/or the sideward scattered light (measured at an angle of <160° may be detected. Herein, forward scattered light may be light detected at an angle of approximately 1800° referred to the excited laser beam, at an angle of approximately 170° referred to the excited laser beam or at an angle of between approximately 160° referred to the excited laser beam. The sideward scattered light may be light detected at any other angle referred to the excited laser beam. Exemplarily, the sideward scattered light may detected at an angle of approximately 30°, 40°, 45°, 70°, 75° and/or 90°. However, the person skilled in the art will notice that the detection at any other angle may also be used in the context of the present invention. The detection may also be performed at varying angles, i.e., at angles varying over time during the method. Alternatively, the detection may also be performed at two or more different angles at the same time. When light scattering in different angles is measured, this may be designated as dynamic light scattering. The excitation may be continuous excitation or may be pulsed excitation, wherein the excitation time is in the range or nanoseconds, microseconds or seconds. Pulsed excitation may be repeated any number of times. The measurement may be performed once or more than once. Exemplarily, the measurement may be repeated two times, three times, four times, five times, ten times, 20 times, 30 times, 40 times, 50 times, 100 times, 150 times, 200 times, 250 times or more often. Exemplarily, one measurement cycle may last less than 1 μs, approximately 10 μs, 0.1 s, 0.5 s, 1.0 s, 1.5 s, 2 s, 5 s, 10 s or longer.

The wavelength and laser intensity may be adjusted in accordance with the sample. As used herein, detection of laser diffraction may be performed by any method known in the art suitable for the detection of light diffraction. In general, light diffraction bases on quantum theory. The wavelength associated with a particle is the de Broglie wavelength:

momentum of the particle($p$)=[Planck's constant($h$)]/[wavelength($\lambda$)]

Herein, for slow-moving particles, the momentum of the particle corresponds to its mass multiplied by its velocity.

As used in the context of the present invention, sedimentation techniques may be understood in the broadest sense as any methods based on the sedimentation of the CPPs of the present invention. A sedimentation technique may be based on natural gravity only or may be expedited by centrifugal force. Preferably, a sedimentation technique in the context of the present invention may be expedited by centrifugal force. Optionally, the volume and/or the weight of the precipitate may be determined, in particular the volume ratio and/or weight ratio of the precipitate and the supernatant may be determined. Alternatively and/or additionally, the sedimentation constant of the precipitates may be determined. Alternatively and/or additionally, the weight density of the precipitates may be determined, such as, e.g., by sucrose gradient centrifugation.

It will be understood that two or more of the methods described above may be combined with another. Further, it will also be understood that two or more of the methods described above may be combined with one or more optical methods.

The excitation light may be any light source known in the art. Preferably, the excitation light is a laser beam or an Hg-lamp.

In a preferred embodiment, the excitation light used in the optical method is a laser beam.

As used in the context of the present invention, a laser may be any laser known in the art. A laser typically shows a comparably high degree of spatial and temporal coherence, unattainable using other technologies. Preferably, the laser light is further monochromatic and/or one laser line is selected for emission. Exemplarily, the laser may be a HeNe or an argon ion laser. A HeNe laser typically emits light of a wavelength of approximately 633 nm, an argon ion laser typically emits light of a wavelength of approximately 488 nm. Laser intensity may be adjusted to the sample. For nephelometry, laser intensity may exemplarily be in the range of from 0.1 to 1000 mW, preferably in the range of from 1 to 100 mW, more preferably in the range of from 10 to 50 mW.

Further, the light emitted by the laser and/or the scattered light may be conducted through one or more filter(s), one or more semipermeable mirror(s) and/or one or more acousto-optical beam splitter(s) and/or may be splitted into particular wavelength(s) by means of one or more prism(s) and/or one or more optical grid(s). Light may be detected by any device known in the art. Exemplarily, the detector(s) may be avalanche photo diode(s) (APD(s)), a photomultiplier tune(s) (PMT(s)) and/or a diode array. A diode array may comprise more than four, more than ten, more than 100, more than 1000 or even more than 10000 diodes.

In a more preferred embodiment, the optical method is performed by detecting light scattering, preferably by dynamic light scattering, more preferably by cross-correlation dynamic light scattering, even more preferably by three-dimensional cross-correlation dynamic light scattering, in particular by nephelometry.

As used herein, detecting light scattering may be detecting static light scattering or detecting dynamic light scattering. Preferably, detecting light scattering is detecting dynamic light scattering.

As used in the context of the present invention, the term "dynamic light scattering" may be understood interchangeably with the terms "photon correlation spectroscopy" and "quasi-elastic light scattering" as technique in physics, which can be used to determine the size distribution profile of small particles in suspension in solution by means of the observance of a time-dependent fluctuation in the scattering intensity. Typically, these fluctuations will occur due to the fact that the small molecules in solutions are undergoing Brownian motion and so the distance between the scatterers in the solution is constantly changing with time resulting in alternating constructive and destructive interference by the surrounding particles. Within this intensity fluctuation, information on the time scale of movement of the scatterers is obtainable.

The dynamic light scattering may be based on any type of light scattering. Typically, this light scattering comprises Rayleigh scattering. Preferably, the emission light is laser. Exemplarily, the dynamic light scattering may be quasi-elastic laser light scattering. Then, the dynamic information of the particles may be derived from an autocorrelation of the intensity trace recorded during the experiment.

In the context of the present invention, the term "cross correlation" may be understood in the broadest sense as a measure of similarity of two waveforms in signal processing. It is commonly used for searching a long-duration signal for a shorter feature.

As used herein, the terms "three-dimensional cross-correlation dynamic light scattering", "3D cross-correlation dynamic light scattering", and "3D dynamic light scattering" may be understood interchangeably.

As used in the context of the present invention, the term "nephelometry" may be understood in the broadest sense as a method performed by measuring the turbidity in an extensively aqueous sample by measuring the light intensity of light passing through the sample at an angle based on the principle that a dilute suspension of small particles will scatter light passed through it rather than simply absorbing it. Nephelometry may be measured manually or in a semi-automated or an automated manner.

In this context, the scattered light may be measured at any angle such as, e.g., at approximately 30°, 40°, 45°, 70°, 75° and/or 90°. Most preferably, the light is detected in a 90° geometry. Typically, the light source is a laser. The results obtained for the sample may optionally be compared to one or more value(s) obtained for calibration samples(s) or may be compared with one or more standard curve(s).

Nephelometry may be end point nephelometry or may be measured over time as kinetic nephelometry. As used herein, end point nephelometry means that the formation or rearrangement is size of the CPPs may be extensively completed and does not or nearly not change any more. In kinetic nephelometry, light scattering is measured over time. Typically, the measurement of light scattering is started right after the calcium and/or phosphate is added and then continued for a certain time. Kinetic nephelometry allows observing changes in the particle size distribution and the average particle size over time. Preferably, nephelometry, as used in the context of the present invention, is kinetic nephelometry. In order to enable the detection of large particles, which may have settled to the bottom of the sample the sample may optionally be shaken or mixed prior to each measurement. As long as the reagent is constant the rate of change can be seen as directly related to the amount of the propensity of the body fluid for calcification.

Alternatively to performing step of determining the transition rate of the transition of primary CPPs into secondary CPPs (step (iii)) by an optical method, it may also be preformed by any other suitable method known in the art. Preferably such method is based on detecting the average size or the average mass of the particles present in the sample.

In the context of the present invention, the step of determining one or more of the rate of the formation of primary and/or secondary CPPs, the amount of primary and/or secondary CPPs and/or the rate of the transition of primary CPPs into secondary CPPs (step (iii)) may also be any other method known in the art, thus, also a non-optical method or a combination of two or more non-optical methods or a combination of one or more optical method(s) and one or more non-optical method(s).

In an preferred embodiment of the present invention the step of determining one or more of the rate of the formation of primary and/or secondary CPPs, the amount of primary and/or secondary CPPs and/or the rate of the transition of primary CPPs into secondary CPPs (step (iii)) is performed by any method selected from the group consisting of:
sedimentation techniques,
filtration analysis,
size exclusion chromatography,
granulometry,
acoustic spectroscopy,
or a combination of two or more thereof.

As used in the context of the present invention, the term "sedimentation technique" may be understood in the broadest sense as any method based on the deposition of the primary and/or secondary CPPs. Preferably, the primary CPPs and the secondary CPPs may bear different sedimentation constants and may, therefore, sediment at different time points. Typically, the secondary CPPs may sediment first. A sedimentation technique of the present invention may be based on gravitational force only or may also include centrifugal force. Preferably, the sedimentation technique of the present invention may also include centrifugal force. A pallet comprising the secondary CPPs and/or the primary CPPs may be formed. Alternatively or additionally, equilibrium centrifugation (e.g., sucrose gradient centrifugation) may be used. Herein, the primary CPPs and the secondary CPPs may be separated from another due to their different mass density. In general, the separated primary CPPs and the secondary CPPs may be investigated further by determining the volume or mass thereof or by observing these via optical methods such as, e.g., microscopy. Optionally, the volume and/or the weight of the precipitate may be determined. In order to observe a kinetic profile of the transition of primary CPPs into secondary CPPs, a number of samples may be investigated.

As used herein, a microscopic method may exemplarily be light microscopy (e.g., brightfield microscopy), fluorescence microscopy (e.g., (confocal) laser scanning microscopy (LSM), stimulated emission depletion microscopy (STED microscopy)), electron microscopy (e.g., scanning electron microscopy (SEM), transition electronic microscopy (TEM), scanning transmission electron microscopy (STEM), scanning tunneling microscopy (STM)), scanning helium ion microscopy (SHIM), scanning probe microscopy (SPM) and/or atomic force microscopy (AFM).

As used in the context of the present invention, the term "filtration analysis" may be understood in the broadest sense as any method based on molecular and/or particulate sieving of the sample. As used herein, the terms "sieving" and "filtrating" may be understood interchangeably. Filtrating may be dead end or continuous filtration. Optionally, filtration may also be cross-filtration. The particles may be separated and/or isolated due to their size. Preferably, the filter has a size allowing the primary CPPs to pass through, whereas the secondary CPPs are retarded. Optionally, the volume and/or the weight of the precipitate may be determined, in particular the volume ratio and/or weight ratio of the precipitate and the supernatant may be determined.

As used in the context of the present invention, size exclusion chromatography may be understood in the broadest sense as any chromatographic method suitable for separating the CPPs of the present invention from the sample of the body fluid. Preferably, the primary CPPs and the secondary CPPs show different elution profiles. Size exclusion chromatography may also be designated as molecular weight chromatography. Optionally, the volume and/or the weight of the precipitate may be determined, in particular the volume ratio and/or weight ratio of the particular fractions may be determined.

As used in the context of the present invention, optical granulometry may be understood in the broadest sense as any method for the optical determination of the size of the particles. In the context of the present invention, optical granulometry will typically be a microscope based method. Optionally, a computer assisted method, preferably based on a binary mask, may be used in order to identify particular structured and characterize and quantify these in size and number. The person skilled in the art will know how to apply a corresponding macro of the present invention. This macro may be run on any suitable computer program such a, e.g., by the open source program ImageJ based on Java.

As used in the context of the present invention, the term "acoustic spectroscopy" may be understood in the broadest sense as any method employing sound for collecting information on the particles that are dispersed in fluid. In the context of the present invention, this sound typically will be ultrasound. Dispersed particles will absorb and scatter ultrasound similarly to light. Acoustic spectroscopy may be based on measuring scattered energy versus angle or measuring the transmitted energy versus frequency. The resulting ultrasound attenuation frequency spectra are the raw data for calculating particle size distribution. One example for acoustic spectroscopy is ultrasound attenuation spectroscopy. The average size of the particles may be determined.

Further, step (iii) of the present invention may also be performed by electroresistance counting. As used in the context of the present invention, electroresistance counting may be understood in the broadest sense as any method based on detecting changes in the electric resistance of the sample. Preferably, the sample is conducted through a thin needle of a size allowing only a single particle or few particles passing through at once. One example of electroresistance counting is the Coulter Counter, which measures the momentary changes in the conductivity of a liquid passing through an orifice that take place when individual non-conducting particles pass through. The particle count is obtained by counting pulses, and the size is dependent on the size of each pulse. Preferably, the passage of one of the larger secondary CPPs will show a stronger signal than the passage of one of the smaller primary CPPs. By setting a certain threshold in size, the number of primary and secondary CPPs may be determined.

Preferably, electroresistance counting is Electrochemical Impedance Spectroscopy (EIS). As used herein, the terms "Electrochemical Impedance Spectroscopy", "EIS", "Impedance Spectroscopy" and "dielectric spectroscopy" may be understood in the broadest sense as a method of measuring the dielectric properties of a medium as a function of frequency based on the interaction of an external field with the electric dipole moment of the sample, often expressed by permittivity. Optionally, the obtained data obtained by EIS may be expressed graphically in a Bode plot or a Nyquist plot.

It will be understood that two or more of the methods described above may be combined with another. Further, it will also be understood that two or more of the non-optical method(s) described above may be combined with one or more optical method(s).

In a preferred embodiment, at least one optical method is combined with electroresistance counting. In a more preferred embodiment, a method based on light scattering is combined with electroresistance counting. In an even more preferred embodiment, a method based on dynamic light scattering is combined with electroresistance counting. In a most preferred embodiment, nephelometry is combined with Electrochemical Impedance Spectroscopy (EIS). This may be performed by any device. Particularly preferably, this is performed by using one or more microfluidic device(s).

Preferably, the employed method(s) may include at least one optical method and/or one acoustical method. More preferably, the method of the present invention includes at least one optical method.

In the context of the present invention, the fluid may be any fluid that may lead to calcification. The fluid may be a body fluid or may be technical fluid.

In a preferred embodiment, the fluid is a body fluid, in particular wherein the fluid is blood, blood plasma, blood serum, lymph and/or urine.

As used herein, the term "body fluid" may be understood in the broadest sense as any fluid obtainable from a body such as, e.g., blood, urine, cerebrospinal fluid, lymph, saliva and/or one or more secret(s) from any gland(s). The term "body fluid" may also include any fluid obtainable from a body after one or more processing step(s) (e.g., centrifugation, filtration, cross filtration, precipitation and/or any other known method for fractioning biological fluids) such as, e.g., blood serum or blood plasma. As used herein, the terms "blood serum" and "serum" may be understood interchangeably. Likewise, the terms "blood plasma" and "plasma" may be understood interchangeably. Preferably, the body fluid is blood, blood plasma, blood serum or lymph.

The body fluid will typically be used directly obtained from the patient or within few minutes or few days. When the samples are stored for more than few hours, the samples may preferably be stored at room temperature or in the fridge. As used in the context of the present invention, the terms "room temperature" and "ambient temperature" may be understood interchangeably. Alternatively, the samples may also be stored in a frozen, deep-frozen or freeze dried state and may then be stored at any temperature below the freezing point, such as, e.g., at −20°, −80° C. or in liquid nitrogen. A freeze-dried powder may also be stored at ambient temperature. Obtaining the body fluid from a patient is typically of no health risk for the patient and can be also conducted by persons who are no medical experts such as, e.g., even the patient at home.

In a more preferred embodiment, the fluid is a body fluid obtained from a patient, preferably wherein said patient has developed calcification and/or is at risk of developing calcification, in particular wherein said patient is a dialysis patient Preferably, the patient who has developed calcification and/or is at risk of developing calcification. has developed calcified plaques and/or is at risk of developing calcified plaques. However, calcification may also be microcalcification or may be calcium precipitation in solution, thus, the formation of any calcium precipitates, optionally including primary and/or secondary CPPs.

The body fluid may be obtained from a patient or may be obtained from a preserved sample or may be artificial body fluid.

As used herein, the term "obtained from a patient" may be understood in the broadest sense as receiving a body fluid from the body of a patient by any means. Exemplarily, blood may be collected from a blood vessel, lymph may be corrected from a lymph vessel, cerebrospinal liquid may be obtained from the cerebrospinal lumen and/or urine and/or sweat may be collected. It will be understood that the body fluid may also be processed further. Exemplarily, blood plasma or blood serum blood may be extracted from the blood by any means known in the art. The body fluid may be used in a method of the present invention or may be stored at appropriate conditions for up to one hour, up to two hours, up to six hours, up to twelve hours, up to a day or even longer. A sample of body fluid stored for more than one day may be designated as a preserved sample.

As used herein, the term "preserved sample" may be understood in the broadest sense as any sample that has been stored for more than more than one day, more than two days, more than a week, more than two weeks, more than a month, more than two months, more than six months or more than a year.

The body fluid sample may be stored as the pure body fluid or may be stored as a sample further comprising other components of the sample as summarized in detail above. In general, all storage conditions suitable for the body fluid may be used. Exemplarily, the body fluid sample may be stored at room temperature, at 4° C., at −20° C., at −80° C. or in liquid nitrogen. Therefore, the body fluid sample may be stored in a liquid or frozen state. Alternatively, the body fluid sample may be stored in a freeze-dried or dried state. The preserved sample may exemplarily be a blood preservation, a serum or plasma preservation, or a lymph preservation.

The patient may be a healthy patient or a patient who is at particular risk of calcification. Preferably, the patient bears an increased propensity for developing calcified plaques. This increased propensity may have congenital and/or acquired reason(s).

As used in the context of the present invention, the term "patient" may be understood in the broadest sense as any subject or individual a body fluid is obtainable from, irrespective, clinical symptoms occur or do not occur. The patient may be any animal, including humans. Preferably, the patient is a mammal, most preferably a human.

The patient who has developed calcified plaques and/or who is at risk of developing calcified plaques may be healthy or may bear a particular risk of calcification. The patient may or may not suffer from any clinical symptoms such as, e.g., hypertonia, diabetes, kidney dysfunction or a rheumatoid disease. Exemplarily, kidney dysfunction may be chronic kidney disease (CKD).

As used herein, the term "body" may be understood in the broadest sense as any living subject or subject that had lived less than ten years ago, less than five years ago, less than four years ago, less than three years ago, less than two years ago, less than one year ago, less than six months ago, less than five months ago, less than four months ago, less than three months ago, less than two months ago, less than one month ago, less than two weeks ago, less than one week ago, less than two days ago, less than one day ago, less than twelve hours ago, less than six hours ago or less than one hour ago. Preferably, the body is the body of any animal including human. An animal is preferably a vertebrate, more preferably an endothermal animal, even more preferably a mammal, most preferably a human.

Optionally, a compound which is a potential or known inhibitor or promoter of calcification may be added to the body fluid. Then, the potency of said compound for inhibiting or promoting calcification may be tested, in particular when a sample comprising said compound is compared with a corresponding sample without the inhibitor. Advantageously, the method of the present invention provides the possibility to characterize the action of the compound in its natural context, i.e., in the body fluid. Inhibitors of calcification are exemplarily Fetuin (e.g., Fetuin-A) and albumin (e.g., serum albumin). In vitro, also chelating agents such as, e.g., ethylenediaminetetraacetic acid (EDTA) or immobilized cation exchanger may be used to inhibit calcification.

Further, in addition or alternatively, phosphate binders may also be used to inhibit calcification. Exemplarily, common phosphate binders comprise aluminium hydroxide (e.g., Alucaps), calcium carbonate (e.g., Calcichew, Titralac), calcium acetate (e.g., Phosex, PhosLo), lanthanum carbonate (Fosrenol), sevelamer (e.g., Renagel, Renvela) and calcium acetate/magnesium carbonate (e.g., Renepho, OsvaRen).

The body fluid may also be an artificial body fluid obtained by admixing and dissolving one or more component(s) is an aqueous solution.

As used herein, the term "dialysis patient" may be understood in the broadest sense as any patient who needs artificial replacement or support for lost or limited kidney function. It will be understood that a dialysis patient is typically a patient of particular risk of developing calcified plaques.

In another more preferred embodiment, the patient suffers from vascular, valvular and/or soft tissue calcification, preferably wherein said patient further suffers from a rheumatoid disease, a malignant disease and/or an infectious disease, in particular wherein the patient shows at least one of the syndromes selected from the group consisting of:
renal dysfunction,
hypertension,
diabetes mellitus,
dyslipidemia,
a lack of adequate mineralization, in particular osteoporosis and/or osteomalacia, and atherosclerosis.

As used in the context of the present invention, the term "rheumatoid disease" may be understood in the broadest sense as any medical problem affecting the joints and connective tissue, typically mainly caused by arthritis. Herein, the terms "rheumatoid disease", "rheumatism", "rheumatic disorder" and "rheumatic disease" may be understood interchangeably. Rheumatoid disease may include but may not be limited to sclerodermia, fibromyalgia syndrome, ankylosing spondylitis, bursitis, tendinitis, wrist, capsulitis, osteoarthritis, psoriatic arthritis, rheumatic fever, rheumatic heart disease, rheumatoid arthritis, systemic lupus erythematosus, temporal arteritis, polymyalgia rheumatic, tenosynovitis, palindromic rheumatism and myositis. However, rheumatoid disease may also include non-articular rheumatism (e.g., regional pain syndrome, soft tissue rheumatism).

As used in the context of the present invention, the term "malignant disease" may be understood in the broadest sense as any malignant disorder known in the. A malignant disease may be a disorder leading to neoplasia, in particular one or more tumour(s). A malignant disease may therefore bean oncolytic disorder including cancer. The term "cancer" may be understood in the broadest sense. It may include the occurrence primary and secondary tumors, metastases and other kinds of pathological neoplasms. However, a malignant disease may also be a non-oncologic disorder such as, e.g., malignant hypertension, malignant hyperthermia, malignant otitis externa, malignant tertian malaria (typically caused by *Plasmodium falciparum*) or neuroleptic malignant syndrome.

An infectious disease may be any infections disease known in the art.

As used herein, the term "syndrome" may be understood in the broadest sense as any association of one or more several clinically recognizable feature(s), sign(s), symptom(s), phenomenum/phenomena and/or characteristic(s) that often occur in the context of a particular disease or disorder, so that the presence of one or more feature(s) may indicate the presence of the disease or disorder. A syndrome may be observed by a medical expert, i.e., by a physician or by a nurse and/or may be observed and potentially reported by the patient.

As used herein, the term "renal dysfunction" may be understood in the broadest sense as any malfunction of the renal system, in particular the kidney(s). Exemplarily, renal dysfunction may be chronic kidney disease (CKD). Optionally, the renal dysfunction may also be nephropathy. The term "nephropathy" as used herein refers to a dysfunction or a non-function of one or both kidneys.

As used herein, the terms "hypertension" and "hypertonia" may be understood interchangeably in the broadest sense as a condition of high blood pressure and is well-known in the art.

As used herein, the terms "diabetes mellitus" and "diabetes" may be understood in the broadest sense as a group of disorders characterized by a failure in regulation of the blood sugar level. It comprises a group of metabolic diseases in which a person has high blood sugar. Typically, diabetes mellitus occurs when the patient's body does not produce enough insulin and/or when cells in the patient's body do not suitable respond to the insulin that is produced. Diabetes mellitus may optionally lead to numerous clinical and non-clinical symptoms such as, e.g., polyuria (frequent urination), polydipsia (increased thirst) and/or polyphagia (increased hunger).

As used in the context of the present invention, the terms "dyslipidemia" and "dyslipidaemia" may be understood interchangeably in the broadest sense as any disorder characterized by an abnormal amount of lipids (e.g. cholesterol and/or triglyceride(s)) in the blood.

As used in the context of the present invention, the term "osteoporosis" may be understood in the broadest sense as a disorder characterized by a reduction of bone mineral density (BMD), deteriorating of bone microarchitecture and/or alteration of the amount and variety of proteins in bone.

As used in the context of the present invention, the term "osteomalacia" may be understood in the broadest sense as a disorder characterized by the softening of the bones. It may be caused by defective bone mineralization secondary to inadequate amounts of available phosphorus and calcium and/or may be caused by an overactive resorption of calcium from the bone as a result of hyperparathyroidism.

As used herein, the terms "atherosclerosis", "arteriosclerosis", "cardiovascular atherosclerosis", "cardiovascular arteriosclerosis" and "cardiovascular plaque" may be understood interchangeably in the broadest sense as the deposition of plaque in the blood vessels. The plaque may be deposited in the lumen of the blood vessels or in the in the middle layer of the walls of medium sized vessels (tunica media). The plaque may comprise calcium salts in combination with other minerals, proteins, fatty acids, triglycerides, cholesterols, low density lipoprotein (LDL), high density lipoprotein (HDL) and/or sugars. Furthermore, cells or cellular fragments such as, e.g., macrophages, red blood cells (RBCs) and platelets, may be part of the plaque. Pathological forms of atherosclerosis may be also designated as arteriosclerotic vascular disease or (ASVD). Cardiovascular plaque may increase the risk of numerous diseases such as hypertonia, myocardial infarction and cerebral apoplexy (stroke). Highly pronounced forms of calcification may further lead to the necessity of amputation of an extremity such as a leg. One of the most pronounced from of atherosclerosis is Mönckeberg's atherosclerosis. The terms "Mönckeberg's atherosclerosis", "Monckeberg's atherosclerosis" and "medial calcific sclerosis" may be used interchangeably. Mönckeberg's atherosclerosis is one of the most severe forms of atherosclerosis. Here, the vessels harden as calcium deposits form in the middle layer of the walls of medium sized vessels (tunica media). As used herein, atherosclerosis may also include calciphylaxis, a severe syndrome of vascular calcification, thrombosis and skin necrosis.

In a preferred embodiment, the fluid is an artificial body fluid and/or an infusion solution.

As used herein, the term "artificial body fluid" may be understood in the broadest sense as any supplement for any body fluid known in the art. Exemplarily, it may be a blood substitute, a plasma substitute or a serum blood substitute. Exemplarily, a blood substitute may comprise but may not be limited to a perfluorocarbon-based blood substitute (e.g., Oxygent (Alliance Pharmaceuticals), Oxycyte (Oxygen Biotherapeutics), PHER-O2 (Sanguine Corp), Perftoran), a hemoglobin-based blood substitute (e.g., Hemopure (Biopure Corp), Oxyglobin (Biopure Corp), PolyHeme (Northfield Laboratories), Hemospan (Sangart), Dextran-Haemoglobin (Dextro-Sang Corp), Hemotech (HemoBiotech)), Fluorasol-DA, HemAssist (Baxter International) or Hemolink (Hemosol, Inc.). Further, a blood substitute may be obtained from stem cells, wherein the stem stems are preferably not human embryonic stem cells. Moreover, dendrimers, biodegradable micelles placental umbilical cord blood or hemerythrin may be used to obtain a blood substitute.

As used herein, the term "infusion solution" may be understood in the broadest sense as any solution suitable for infusion known in the art. Exemplarily, an infusion solution may be an isotonic electrolyte solution, isotonic saline, isotonic full electrolyte solution, glucose solution, Ringer' solution or a colloidal solution. It will be understood that an infusion solution may further bear one or more pharmaceutically active agent(s), one or more pharmaceutically acceptable carrier(s) or excipient(s). In general, the infusion solution may comprise any pharmaceutically acceptable component, may it be charged or uncharged, polar or non-polar, a high-molecular weight or a small molecule.

It will be understood that an artificial body fluid or an infusion solution may or may not comprise any inhibitor(s) or promoter(s) for calcification known in the art. It may comprise said inhibitor(s) or promoter(s) for calcification naturally or said inhibitor(s) or promoter(s) of calcification may be added to such artificial body fluid or infusion solution. Typically, the technical fluid may comprise any inhibitor(s) for calcification known in the art. Exemplarily, such calcification inhibitor may be a fetuin polypeptide (e.g., fetuin-A) and albumin (e.g., serum albumin), a chelating agent such as, e.g., ethylenediaminetetraacetic acid (EDTA), an immobilized cation exchanger or a phosphate binder (e.g., aluminium hydroxide (e.g., Alucaps), calcium carbonate (e.g., Calcichew, Titralac), calcium acetate (e.g., Phosex, PhosLo), lanthanum carbonate (Fosrenol), sevelamer (e.g., Renagel, Renvela), calcium acetate/magnesium carbonate (e.g., Renepho, OsvaRen)).

In another preferred embodiment, the fluid is a technical fluid, preferably wherein said fluid is an aqueous fluid, in particular wherein said fluid is an industrial process fluid, a fluid comprising a laundry agent or a dishwashing agent, a soap sud, a shower bath, a bath additive, a cooling fluid, a comestible good or is intended to be used for the production of a comestible good.

As used herein, the term "technical fluid" may be understood in the broadest sense as any fluid that is usable in the context of industrial facilities, comestible good production and/or domestic purposes. A use in an industrial facility may, e.g., be the use as industrial process fluid, as a general purpose cleaner, as a water additive (e.g., as a water softener) or as cooling agent. A use for comestible good production may comprise cooking, baking, roasting, frying, condensation, thickening, conservation, drying, freeze-drying, infusing, distilling. A comestible good may comprise, but may not be limited to a beverage (e.g., water, juice, lemonade, an infused drink (e.g., coffee, tea), an instant beverage (e.g., instant coffee, instant tea), milk, bear, vine, liquor, hard liquor), foodstuff (e.g., bakery goods (e.g., bread, cake, biscuits), sweets, fruit an instant food (e.g., pocket soup). A fluid for domestic purposes may exemplarily be a laundry agent, a dishwashing agent, a soap sud, a shower bath, a toilet cleaning agent, a softener, a rinsing agent, an impregnating agent, a bathroom cleaner, a general purpose cleaner, a water additive (e.g., a water softener) or a bath additive.

The technical fluid may or may not comprise detergents and may or may not be used to clean laundry, dishes or other domestic goods. Further, the fluid may also be a domestic cleaning agent, a WC cleaning agent, an aquarium cleaning agent or any water additive known in the art to prevent or promote calcification. Alternatively, the technical fluid may be used in the context of an industrial facility. Typically, the technical fluid is intended to avoid calcification in the form of residuals comprising calcium salt either in liquid or in dried form. This may be of particular importance as thin tubes or pipes are used. Further, this may be of particular importance as water bearing a high hardness degree is used.

The method of the present invention may be performed at a varying temperature, following a particular temperature profile or at a constant temperature.

As used herein, the term "industrial process fluid" may be understood in the broadest sense as any fluid used in any industrial process that may bear a propensity for calcification. Preferably, the industrial process fluid may be industrial process water. As used herein, the terms "industrial process water", "industrial water", "process water" "service water" and "processing water" may be understood interchangeably. Exemplarily, an industrial process fluid may be used as a cooling fluid, as a cleaning fluid, for desalting or as fluid used in a turbine (e.g., a steam turbine).

It will be understood that a technical fluid may or may not comprise any inhibitor(s) or promoter(s) for calcification known in the art. It may comprise said inhibitor(s) or promoter(s) for calcification naturally or said inhibitor(s) or promoter(s) of calcification may be added to such technical fluid. Typically, the technical fluid may comprise any inhibitor(s) for calcification known in the art. Exemplarily, such calcification inhibitor may be a fetuin polypeptide (e.g., fetuin-A) and albumin (e.g., serum albumin), a chelating agent such as, e.g., ethylenediaminetetraacetic acid (EDTA), an immobilized cation exchanger or a phosphate binder (e.g., aluminium hydroxide (e.g., Alucaps), calcium carbonate (e.g., Calcichew, Titralac), calcium acetate (e.g., Phosex, PhosLo), lanthanum carbonate (Fosrenol), sevelamer (e.g., Renagel, Renvela), calcium acetate/magnesium carbonate (e.g., Renepho, OsvaRen)).

In a preferred embodiment, said method is performed at a constant temperature and/or at a constant pH.

As used herein, the term "constant" means that the temperature remains extensively the same during step (iii) of the method of the present invention. Most preferably, the difference in temperature between samples to be compared with another should be less than 5° C., less than 4° C., less than 3° C., less than 2° C., less than 1° C., less than 0.5° C., less than 0.25° C. or even less than 0.1° C. Preferably, the constant temperature may be in the range of from 0° C. to 100° C., more preferably in the range of from 0° C. to 45° C., even more preferably in the range of from 4° C. to 42° C., even more preferably in the range of from 20° C. to 40° C., even more preferably in the range of from 36° C. to 38° C., even more preferably in the range of from 36.0° C. to 37.5° C. and most preferably in the range of from 36.5° C. to 37.0° C. Optionally, the used device may comprise a temperature sensor.

As used herein, the pH (potentia hydrogenii) may be understood as commonly understood in the art, i.e., as the negative decimal logarithm of the hydrogen ion activity in a fluid.

As used herein, the term "constant" means that the pH remains extensively the same during step (iii) of the method of the present invention. Most preferably, the difference in pH between samples to be compared with another should be less than 3 pH units, less than 2 pH units, less than 1 pH unit, less than 0.8 pH units, less than 0.6 pH units, less than 0.4 pH units, less than 0.2 pH units, less than 0.1 pH units or less than less than 0.05 pH units. The pH may be adjusted at any pH. Preferably, the pH may be at an extensively neutral pH, i.e., between pH 5.5 and pH 8.0, more preferably between pH 6.0 and pH 8.0, even more preferably between pH 6.5 and pH 7.8, even more preferably between pH 7.2 and pH 7.6, most preferably at a physiological pH, i.e. at a pH at approximately pH 7.4.

As mentioned above, the sample is preferably a fluid sample. The method may be performed in any device suitable to perform the method of the present invention. It will be understood that the choice of the carrier will depend on the specific method. Exemplarily, the method may be performed using one or more cuvette(s), using one or more microscopic slide(s), using a multiwell format, using a microarray, using one or more plastic reaction tube(s), using one or more glass vial(s), using a chromatographic column, using a syringe, using a needle or using a combination of two or more thereof. It will be understood that the surface of the used device should not or nearly not interfere with the method, thus, in particular with the propensity for calcification.

In a preferred embodiment, the method is performed in one of the following:
(a) a multiwell format, more preferably in an 8-well chamber plate, in a 16-well chamber plate, in a 96-well microtiterplate or in a 384-well microtiterplate, in particular in a 96-well microtiterplate;
(b) a flow-through cell; or
(c) a microfluidic device.

As used herein, the term "flow-through cell" may be understood in the broadest sense as a device wherein the sample of the body fluid is conducted through whereat the propensity for calcification is determined. Herein, the flow may be a steady flow or may be interrupted for measurement.

The data obtained from the method of the present invention may be analyzed manually, semi-automatically or automatically.

In general, the method may be performed offline or online.

As used herein, the term "offline" may be understood in the broadest sense as any method wherein a body fluid sample is provided in a first step (e.g., the patient's body, a preserved sample, or a sample of a technical fluid) and steps (i) to (iii) of the method of the present invention are performed subsequently. Then, the method is performed batchwise. Exemplarily, the propensity for calcification of a body fluid obtained from a dialysis patient may be diagnosed offline before, while or after the patient's blood circulation is connected with the dialysis machine. The same may apply for a sample measured offline before used in a technical device (e.g., a cooling fluid used in a cooling circuit or a laundry agent in a washing machine).

As used herein, the term "online" may be understood in the broadest sense as any method wherein the provision of the body fluid sample and steps (i) to (iii) of the method of the present invention are performed extensively simultaneously. Then, the body fluid is provided, conducted through a device and simultaneously measured. Herein, the flow may be a steady flow or may be interrupted for measurement. Optionally, the body fluid is extracted directly from a patient. Optionally, the analyzed body fluid or a fraction thereof is conducted back into the patient's body. An online devise may optionally even be incorporated into the patient's body. The same may apply for a sample measured online from a technical device (e.g., a cooling circuit). Typically, an online measurement is a measurement over time. Exemplarily, the propensity for calcification of a body fluid obtained from a dialysis patient may be diagnosed online when the patient's blood circulation is connected with the dialysis machine. The method of the present invention may then be performed automatically or semi-automatically. The dialysis machine may even comprise a device performing the method of the present invention as an intrinsic unit or as an add-on.

The measurement may be performed over time or may be a measurement at the end point. Preferably, the measurement is a measurement over time.

As used in the context of the present invention, the term "over time" may be understood in the broadest sense as any measurement, wherein measurements are performed in one sample at different time points. A measurement over time may also be designated as a kinetic measurement. Exemplarily, the measurement over time may be kinetic nephelometry. The person skilled in the art will notice that the time interval chosen between two measurements will typically depend on the rate of the formation and/or rearrangement of particles. In order to determine fast formation and/or rearrangement of particles the person skilled in the art will typically chose short time intervals, whereas he will typically chose longer time intervals for slower processes. The time intervals may typically be in the range of few minutes up to several hours. As mentioned above, the rate will typically depend on the inserted concentrations and dilutions. Exemplarily, a measurement may be performed over a total time of several seconds, several minutes, several hours, several days or even several weeks. Preferably, in the context of measurement over time, the measurement is started right after the calcium and/or phosphate is added. As long as the reagent is constant the rate of change can be seen as directly related to the amount of the propensity of the body fluid for calcification. In order to also detect the large particles, which may have settled to the bottom of the sample the sample may optionally be shaken or mixed prior to each measurement.

As used herein, the term "end point" may be understood in the broadest sense as a measurement at a time point on which the formation or rearrangement is size of the CPPs is extensively completed and does not or nearly not change any more. In order to also detect the large particles, which may have settled to the bottom of the sample the sample may optionally be shaken or mixed prior to measurement.

The method of the present invention may be performed by any principle suitable for this method known in the art. The step of determining the transition rate of the transition of primary CPPs into secondary CPPs (step (iii)) may be performed by any method known in the art. Preferably such method is based on detecting the average size or the average mass of the particles present in the sample.

As used herein, the term "microfluidic device" may be understood in the broadest sense as any miniaturized diagnostic tool. The microfluidic device may be any microfluidic device known in the art suitable in the context of the present invention. The microarray may also be understood as a lab-on-a-chip. Typically, the microfluidic device will be a two dimensional array on a solid substrate such as, e.g., a glass slide, a ceramic slide, a metal slide, a silicon thin-film cell, a plastic slide or a compact disc (CD) format. In order to enable the optical method of the present invention, at least a part of the microfluidic device may preferably be permeable for the light used for the method of the present invention. The micro fluidic device may comprise one or more microfluidic channel(s) and/or chamber(s). These channels may also be used for mixing the sample. In a microfluidic device one or both of the processes of formation of primary and/or secondary CPPs and the transition of primary CPPs into secondary CPPs may be accelerated. The microfluidic device may also be a flow-through cell. A microfluidic device may also be a diagnostic medical dipstick, in particular in the context of urine as a fluid.

The method may be performed manually, semi-automatized or automatized.

In a preferred embodiment, at least the step of determining one or more of the rate of the formation of primary and/or secondary CPPs, the amount of primary and/or secondary CPPs and/or the rate of the transition of primary CPPs into secondary CPPs (step (iii)) is automated, more preferably at least the step of incubating said sample at conditions allowing the formation of calciprotein particles (CPPs) and the step the determining the transition rate of the transition of primary CPPs into secondary CPPs (steps (ii) and (iii)) are automated, in particular all of the steps (i), (ii) and (iii) are automated.

As used in the context of the present invention, the terms "automated" and "automatized" may be understood interchangeably in the broadest sense as the use of any control system(s) and/or information technology/technologies, in particular computer-assisted process(es), to reduce the need for human work in the method. Exemplarily, automatization as used herein may comprise the use of automatic pipettes and/or computer-assisted readout methods. Optionally, automatization may even include computer-assisted experimental design and/or computer-assisted analysis of the obtained data. Graphical display of the obtained results may also be included.

In a preferred embodiment, the primary CPPs have an average diameter smaller than 100 nm and the secondary CPPs have an average diameter of larger than 100 nm.

More preferably, the size of primary CPPs is in the range of between 50 nm and 100 nm, most preferably in the range of about 60 nm to 75 nm. The secondary CPPs may more preferably have a size in the range of between 100 nm and 500 nm, most typically in the range of about 100 nm to 200 nm. However, as mentioned above it will be understood by a person skilled in the art that the size of the primary CPPs as well as the size of the secondary CPPs will typically depend on the specific concentrations and conditions used in the method.

The transition rate of the transition of primary CPPs into secondary CPPs determined for the body fluid may be analyzed by comparing different body fluid samples with another or may be compared with one or more calibration sample(s).

In a preferred embodiments, one or more of determining the rate of the formation of primary and/or secondary CPPs (a), determining the amount of primary and/or secondary CPPs (b) and/or determining the rate of the transition of primary CPPs into secondary CPPs (c) step (iii) is/are compared with one or more control sample(s).

As used in the context of the present invention, the term "control sample" may be understood in the broadest sense as any sample that is usable as a reference sample. As used herein, the terms "control sample" and "calibration sample" may be understood interchangeably. The control sample may be standardized sample (e.g., a sample with known properties) or may be an intrinsic control, i.e., one of the samples tested. Typically, under extensively identical reaction conditions (e.g., measured at extensively the same temperature, in extensively the same buffer, at extensively the same pH, with extensively the same concentrations of soluble calcium salt and soluble phosphate salt) and the employment of an extensively identical method, the control sample also will show extensively identical results. The propensity for calcification of the sample(s) in question and the control sample(s) may be measured concomitantly in assay (e.g., on one microtiter plate or on or in one microfluidic device), may be measured subsequently on the same day (e.g., in a cuvette) or may be even measured on different days (e.g., the device used for determining the propensity of calcification has been calibrated by a control sample or is calibrated by a control sample afterwards).

The use of a control sample may lead to the standardization of the measurement and, thus, renders the method device-independent as the obtained results are compared with and referred to this control sample on the device the measurement is also conducted on. Changes may then be quantified as changes relative to the control sample. The calibrations sample(s) may comprise one or more body fluid(s) or may be an artificial sample. Optionally, an artificial sample may bear a defined concentration of inhibitors of the transition of primary CPPs into secondary CPPs such as, e.g., a fetuin polypeptide (e.g., fetuin-A) or an albumin polypeptide (e.g., serum albumin).

When the fluid is a body fluid, the control sample in the context of the present invention may preferably be a sample obtained from a healthy patient. When the fluid is a technical fluid, an artificial body fluid or an infusion solution, the control sample in the context of the present invention may preferably be a sample bearing acceptable calcification propensity. In case the propensity for calcification is considerably higher than that obtained for the control sample, this may indicate that the propensity for calcification is undesirably high and that further actions (e.g., the administration or use of calcification inhibitors) may optionally be desired. In case the propensity for calcification is considerably lower than that obtained for the control sample, this may indicate that the propensity for calcification is undesirably low and that further actions (e.g., the administration or use of calcification promoters, calcium and/or phosphate) may optionally be desired.

The data obtained from any method(s) of the present invention may be analyzed by any measure known in the art.

In a preferred embodiment, determining the rate of the transition of primary CPPs into secondary CPPs (c) of step (iii) is determined by determining the time point of half maximal transition time ($T_{50}$) of the transition of primary CPPs into secondary CPPs.

As used in the context of the present invention, the term "half maximal transition time" or "$T_{50}$" may be understood in the broadest sense as the time point wherein half of the transition (50% transition) of primary CPPs into secondary CPPs is accomplished. The dimension of the $T_{50}$ is time, thus, given in the unit second (s or sec), minute (min), hour (h), day (d), week (w), month or year (a). Most typically, the $T_{50}$ will be given in minutes.

The $T_{50}$ value may be determined by plotting the measured light scattering of the sample (e.g., in Relative Nephelometric Units (RNU)) against the time (e.g., in [min]), exemplarily by plotting an XY-graph (cf., FIG. 1B.). The plotted data may be fitted by a nonlinear regression (e.g., in a log(agonist) vs. response—variable slope). Then, the light scattering in the sample in which only primary CPPs are present is determined as well as the light scattering in the sample in which only secondary CPPs are present. The arithmetic mean between light scatterings is calculated. Finally, the time point ($T_{50}$) in which the overall light scattering represents such arithmetic mean is determined. In this context, the $T_{50}$ value may also be designated as $RNU_{T50}$ value.

The method of the present invention may optionally further comprise the calculation of the hydrodynamic radius (Rh) from the second order cumulant fits via the Stokes-Einstein equation well-known in the art. Then, the $T_{50}$ value may also be determined by plotting the determined average diameter sizes of the CPPs in the sample (e.g., in [nm]) against the time (e.g., in [min]), exemplarily by plotting an XY-graph (cf., FIG. 1A). The plotted data may be fitted by a nonlinear regression (e.g., in a log(agonist) vs. response—variable slope). Then, the average particle size of primary CPPs and the average particle size of secondary CPPs are determined. The arithmetic mean between the average particle size of primary CPPs and the average particle size of secondary CPPs is calculated. Finally, the time point ($T_{50}$) in which the average particle size of all CPPs represents such arithmetic mean is determined.

Plotting the data, fitting of the data and/or calculating the $T_{50}$ (or $RNU_{T50}$) value(s), may be performed manually or may be preformed by a computer-assisted method. The computer-assisted method may be performed by any suitable program, e.g., by Excel® and/or GraphPad Prism®.

The method of the present invention may be used for scientific, industrial and/or clinical purposes. Exemplarily, it may be used to obtain more information on the interaction between congenital and/or acquired predisposition of the propensity for calcification in a patient. Further, the method may also be used to identify and characterize calcification inhibitors and promoters. The method may even be used for the primary and/or secondary screening of compounds in order to determine their influence on calcification. This screening may be a cell-free screening and optionally a high-throughput screening.

In the context of identifying and characterizing calcification inhibitors and promoters, an inhibitor or promoter may be administered to a patient or may be admixed to the body fluid in vitro. When the inhibitor or promoter may be administered to a patient, then, after a certain time, a sample from said patient is obtained and tested by the method of the present invention. When inhibitor or promoter is admixed to the body fluid in vitro, then the sample is incubated for a certain time after admixing the inhibitor or promoter and, subsequently, the method of the present invention is conducted.

The method of the present invention may serve to identify unknown calcification inhibitors and promoters and to test already known characterize calcification inhibitors and promoters in more detail. Further, the interplay between different one or more inhibitor(s) and/or one or more promoter(s) may be investigated. The inhibitor(s) and promoter(s) may be compound(s) active in a patient or in a medical product or composition (e.g., a blood preservation, at the surface of a medical device). Alternatively, the inhibitor(s) and promoter(s) may also be compound(s) active in a non-medical context. Exemplarily, inhibitor(s) of calcification may be used in consumer goods (e.g., laundry agents, dishwashing agents, domestic cleaning agents, toilet cleaning agents, aquarium cleaning agents etc.) and water additive(s).

Moreover, the method of the present invention may also be used to determine the risk of a patient for developing calcification. Then, the doctor and/or medicinal staff may obtain more information on whether and how the patient should be treated with calcification inhibitors, thus, is able to make informed therapy decisions.

The following figures and examples are intended to illustrate the invention but not to limit the scope of protection conferred by the claims.

EXAMPLES

Methods

Sampling and Preparation of Serum Specimens

Figure 1A:
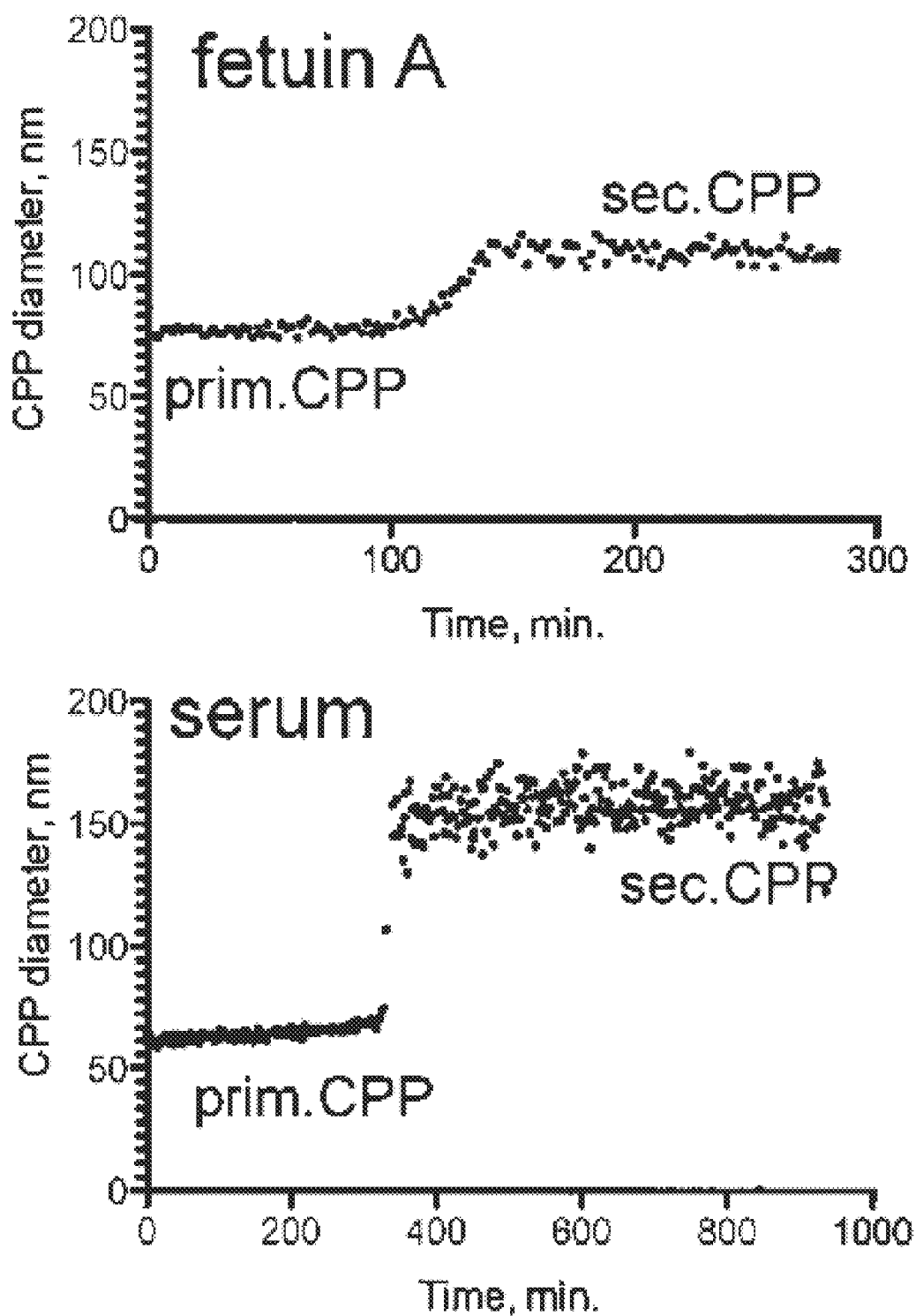
FIG. 1. Detection of CPP transition. (A) 3D-DLS detection of CPP transition in the presence of fetuin-A and human serum. (B) Nephelometry detection of CPP transition in the presence of human serum. (C) Gross visual appearance of the standard nephelometer assay serum solutions containing CPPs in solution (above) and after sharp centrifugation of the solutions (below). Experiment was performed at 3rC in standard photometry vials and with the same solutions used in the respective proportions as in the final nephelometer assay. (D) Pellets after centrifugation of the solutions.

Venous blood from eight healthy volunteers was taken in Sarstedt Monovette® vials. After clotting for 30 min, the samples were centrifuged at 3,000×g for 10 minutes at room temperature. Serum from all individuals was pooled and aliquoted. Blood from 10 to 16 week old DBA/2 fetuin-A knock-out, heterozygous and wildtype mice (Sch äfer et al., 2003; Jahnen-Dechent et al., 1997), was sampled from the heart at the time of sacrifice.

Blood from male Wistar rats (Charles River, Sulzfeld, Germany), which had received food supplemented with 0.75% adenine and calcium 1.05%, phosphorus 0.8%, protein 18.5% for four weeks to induce uremia and vascular calcifications, was taken at sacrifice at age 16 weeks from the inferior vena cava (Pasch et al., 2008). Likewise, control blood was taken from healthy, nonuremic, non-calcified rats of the same age and gender, which had been treated with sodium thiosulfate (0.4 g/kg body weight) in normal (0.9%) saline i.p. three times a week for 6 weeks. Of note, sodium thiosulfate ($Na_2S_2O_3$) did not have any impact on the assay when spiked to serum in amounts of up to 40 mM.

After clotting at room temperature, blood samples from humans, mice or rats were spun at 3,000×g for 10 minutes at room temperature to separate serum from blood cells. The serum was shock frozen in liquid nitrogen and stored at −80° C. Before use in the nephelometer assay, samples were thawed, and centrifuged at 10,000×g for 30 min at room temperature to remove potential small particles which might have formed during the freezing and thawing of samples (cryoprecipitates) and which might interfere with the assay by providing precipitation-accelerating niduses.

Devices, Plastic Materials and Chemicals

The Nephelostar® nephelometer was purchased from bmg labtech, Offenburg, Germany, the Liquidator96™ bench-top pipetting system was purchased from Mettler Toledo GmbH, Giessen, Germany. 96-well plates were from Brand GmbH, Wertheim, Germany, and 96-well plastic Covers from Carl Roth GmbH, Karlsruhe, Germany. All chemicals (e.g., NaCl, Hepes, $CaCl_2$, $NaH_2PO_4$, $Na_2HPO_4$ and NaOH) were purchased from AppliChem, Darmstadt, Germany, in "pro analysis" grade quality.

Protein Quantification

For quantification of proteins in solutions, the Pierce BCA Protein Assay Kit was used according to the manufacturer's instructions. BSA (2 mg/ml, Pierce) was used as a standard. Western blots were performed according to standard protocols with SDS-PAGE (4%-12%), with 1 mg protein or 0.4 mg pure fetuin-A or albumin loaded per lane. The following primary antibodies against fetuin-A and albumin were used: polyclonal rabbit anti-human fetuin-A antiserum 5359 (Behring AG, Marburg, Germany) and mouse anti-human albumin (1:2500, catalog number 0300-0080; AbD Serotec). For fluorescence detection, the following horseradish peroxidase-coupled secondary antibodies were used: swine anti-rabbit IgG (1:5000, catalog number P0217; Dako) and rabbit anti-mouse IgG (1:2000, catalog number P0260; Dako). Protein stains were performed with the Imperial Protein Stain according to the manufacturer's instructions (Thermo Scientific); 6.0 mg total protein or 2.5 mg pure fetuin-A or albumin was loaded per lane.

Three-Dimensional Cross-Correlation Dynamic Light Scattering (3D-DLS)

Multiple scattering in Solutions with high particle density prevents the characterization by Standard dynamic lightscattering methods. Therefore we used a 3D cross-correlation dynamic light scattering (3D-DLS) setup for the analysis of turbid CPP samples. 50-52 Measurements were performed using a Standard light scattering device (ALV GmbH, Langen, Germany) with He—Ne-laser (JDS Uniphase, Koheras GmbH, 632.8 nm, 25 mW, Type LGTC 685-35), two avalanche photodiodes (Perkin Eimer, Type SPCM-AQR-13-FC) and an ALV 5000 correlator. The scattered light was detected at 90° geometry. The sample temperature was adjusted by an external thermostat equipped with a Pt-100 temperature sensor. The hydrodynamic radius Rh was calculated from second-order cumulant fits via the Stokes-Einstein equation. Measurements covered a time span of 1400 minutes in 2 minute intervals. Previous TEM investigations revealed that aged, secondary CPPs have an ellipsoidal shape with an axes ratio of approximately b/a z 0.3. For the sake of clarity, we calculated the hydrodynamic radii, not the semi-axes, to characterize the individual CPP stages.

Nephelometer Assay

Three-dimensional cross-correlation dynamic light scattering (3D-DLS) is a method, which detects laser scatter in solutions and integrates these data to yield Information about the development of particle size over time.

Stock Solutions: 1. NaCl-solution: NaCl 140 mM, 2. Calcium solution: $CaCl_2$ 40 mM+Hepes 100 mM+NaCl 140 mM, pH adjusted with NaOH 10 mM to 7.40 at 37° C., 3. Phosphate solution: $Na_2HPO_4$ 19.44 mM+$NaH_2PO_4$ 4.56 mM+Hepes 100 mM+NaCl 140 mM, pH adjusted with NaOH 10 mM to 7.40 at 37° C. Preparation of 96-well plates: all Solutions were pre-warmed to 34.5° C. in a thermo constant room where also all pipetting steps were performed with the liquidator96™ bench-top pipetting System using a set of new pipetting tips for every pipetting step.

These pipetting steps were performed in the following order: 1. NaCl-solution: 20 µl/well, 2. serum 80 µl/well, 3. shaking for 1 minute, 4. phosphate solution 50 µl/well, 5. shaking for 1 minute, 6. calcium solution 50 µl/well, shaking for 1 minute. Air bubbles in the wells were disintegrated with a pocket lighter and the 96-well covered with a ThinSeal™ adhesive sealing film for microplates. As line, A" of the 96-well plate often showed unreliable results, it was generally left out. Assay conditions and Nephelostar® settings: measurement in a thermo constant room at 34.5° C. with the internal radiation of the device turned off. This led to an infernal measurement temperature of 36.5° C. to 37° C. The Nephelostar® was operated and controlled via the Nephelostar provider's Galaxy Software on a Windows Computer platform. The assay was performed with 200 cycles of 1.5 seconds measurement time per well and a position delay of 0.1 seconds in horizontal plate reading mode, adding up to a cycle time of 180 seconds/cycle for our Standard assay. This adds up to a total assay run time of 10 hours per assay. For some measurements, the cycle time was extended to 360 or 540 seconds, which adds up to assay times of 20 and 30 hours, respectively. The gain and laser adjustment was set at 90% required value, gain 50 with a laser beam focus of 1.5 mm and a laser intensity of 50%.

Data Processing

After completion of the run, data were transferred to Excel® and transposed from lines into columns. Data columns were copied into the GraphPad Prism® program to generate an XY-graph. Data were then processed by calculating nonlinear regression in the "log(agonist) vs. response—variable slope (four Parameters)" mode using the "robust fit" fitting method. The resulting values obtained for $T_{50}$ and $RNU_{T50}$ were further processed as required.

Results

Here, we tested whether primary CPPs would also be generated when human serum instead of fetuin-A solution was used (FIG. 1A, lower part). Indeed, in both cases primary CPPs of comparable size (diameter about 50 nm) were generated, which underwent spontaneous transition to secondary CPPs (diameter about 150 nm), albeit within very different time frames (FIG. 1A). Given these grossly different transition times, we reasoned that the delay of the transition might reflect the stability of primary CPPs and that measuring this step might provide a quantitative estimate for the calcification inhibitory propensity inherent in serum.

Figure 1B:
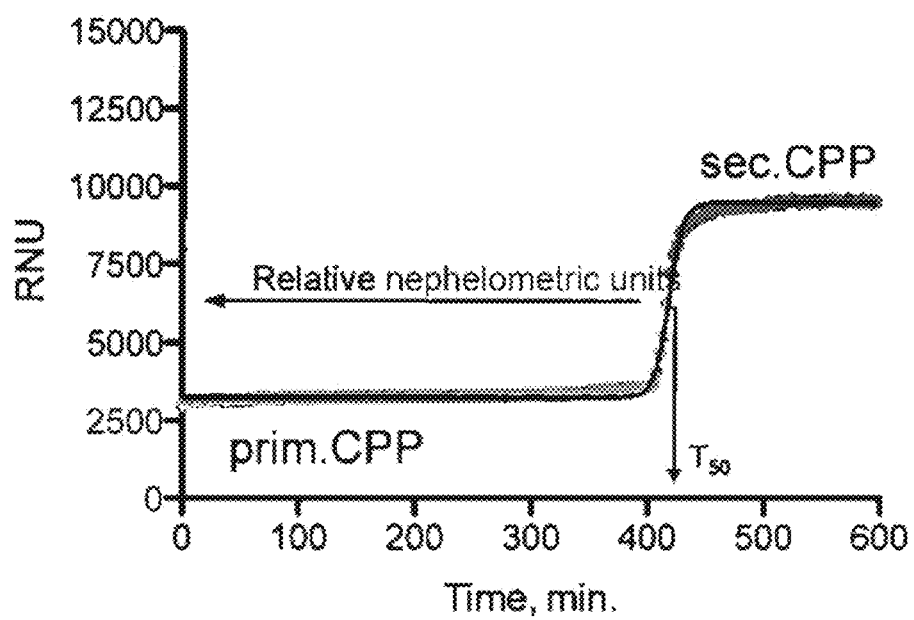
Figure 1C:
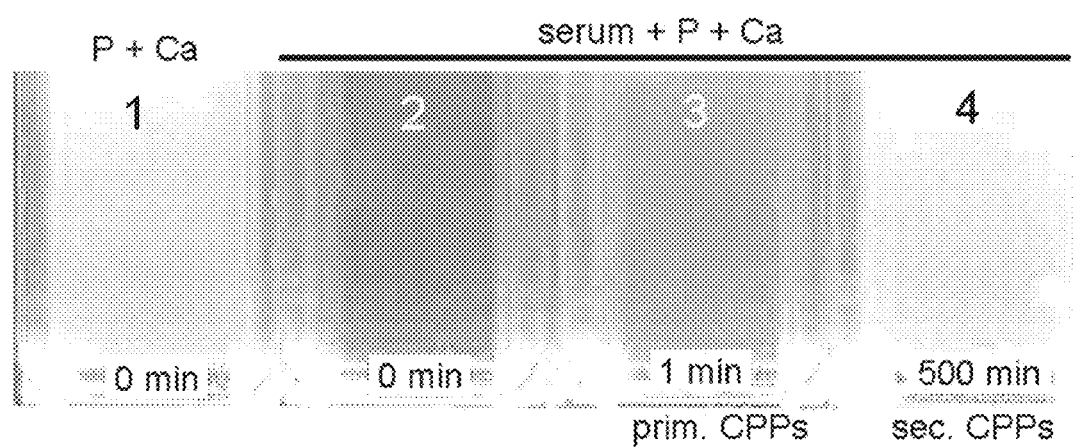
Figure 1D:
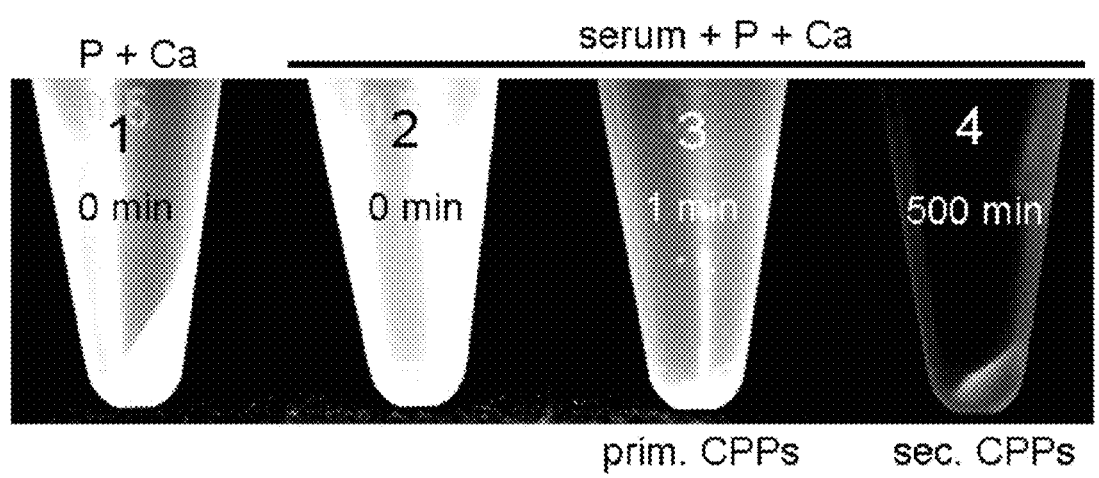

As 3D-DLS is not widely available and can measure only one sample per day, we aimed to establish a practical and broadly applicable alternative assay for the detection of the mentioned transition step. Nephelometry is based on the same principles as DLS and quantifies the amount of laser light scatter in turbid solutions. Consequently, the transition was also detectable by nephelometry (FIG. 1B), and it is of note even visible to the naked eye (FIG. 1C).

For the establishment of the nephelometry-based assay, we took advantage of the automated laser-based microplate nephelometer Nephelostar® which we run in the 96-well-plate mode. The resulting data were analyzed using Excel® and GraphPad Prism® Software to yield nonlinear regression curves and the resulting values of half maximal transition time ($T_{50}$, FIG. 1A)) and of Relative Nephelometric Units ($RNU_{T50}$, FIG. 1B) at this point in time were determined.

We chose physiological conditions for temperature (37° C.) and pH (7.40 at 37° C.), and designed the assay for a final volume of 200 µl per well. These 200 µl consisted of 20 µl NaCl 140 mM, 80 µl serum, 50 µl phosphate 24 mM and 50 µl calcium 40 mM solution which were mixed in this order.

The phosphate and calcium Solutions were supplemented with NaCl 140 mM and Hepes 100 mM, the pH was adjusted to 7.40 at 37° C. This mixture resulted in the final concentrations as depicted below:

$Ca^{2+}$: 10 mM
$PO_4^{2-}$: 6 mM
NaCl: 140 mM
Hepes: 50 mM
at a pH 7.40 and 37° C.

Figure 2A:
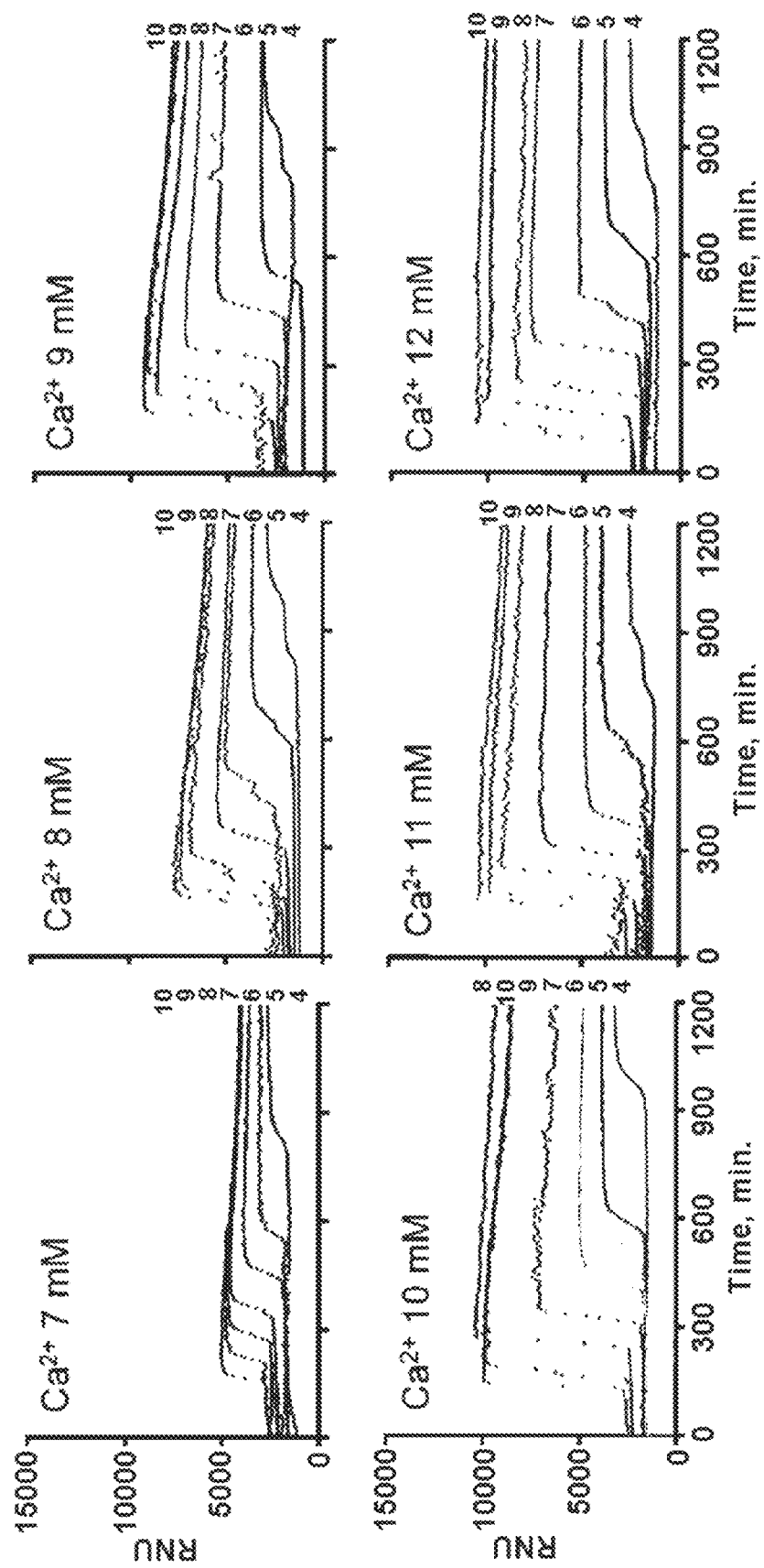
FIG. 2. Determination of nephelometer assay conditions. (A) Impact of varying calcium and phosphate concentrations. Calcium 10 mM and phosphate 6 mM were finally chosen as standard concentrations for the assay. (B) Temperature-dependence of pH. Calcium or phosphate solutions buffered by Hepes or Tris were heated from room temperature to 40° C. and the pH values recorded. The less temperature sensitive Hepes buffer was chosen for the assay. (C) Impact of pH. Calcium and phosphate solutions adjusted to pH values from 7.1 to 7.6 were tested. A pH of 7.40 at 37° C. was chosen for the assay. (D) Impact of amount of serum. Serum amounts from 60 µl to 100 µl were tested (with NaCI 140 mM replenishing the missing volume to an amount 200 µA in all vials), and 80 µA serum finally chosen for the assay.

The 20 µl NaCl were introduced as an extra volume usable for spiking experiments. A wide range of calcium and phosphate concentrations were systematically tested (FIG. 2A) and final concentrations of calcium 10 mM (i.e. 40 mM in stock solution) and phosphate 6 mM (i.e. 24 mM in stock solution) finally chosen in our assay for three reasons: (i) the transition occurred in a central position in the time- and RNU coordinate system leaving space for changes into all directions, (ii) these concentrations represent the numerically optimal relation of calcium and phosphate with regard to the formation of hydroxylapatite, (iii) our previous experiments investigating CPPs have been performed with these concentrations.

Figure 2B:
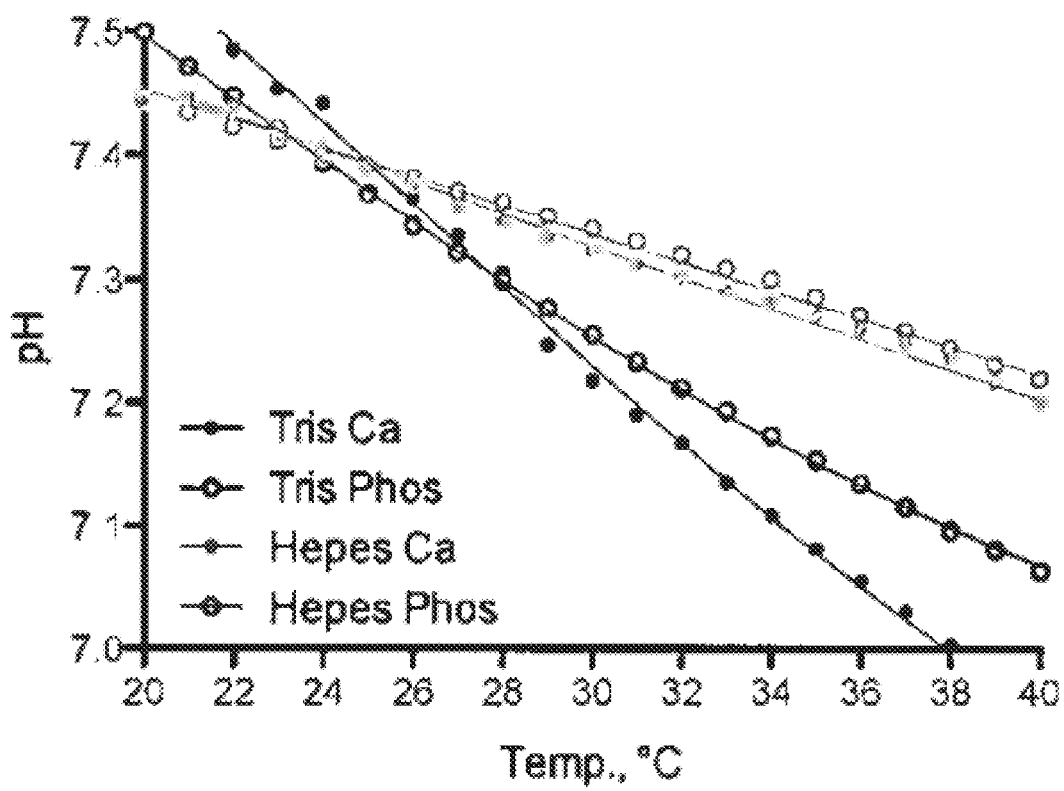
Figure 2C:
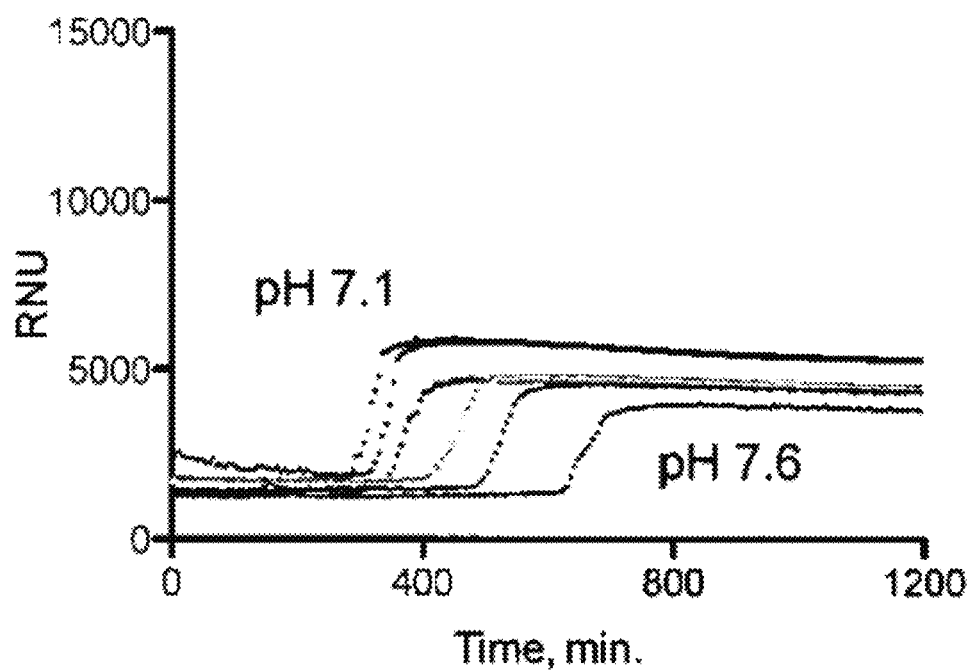
Figure 2D:
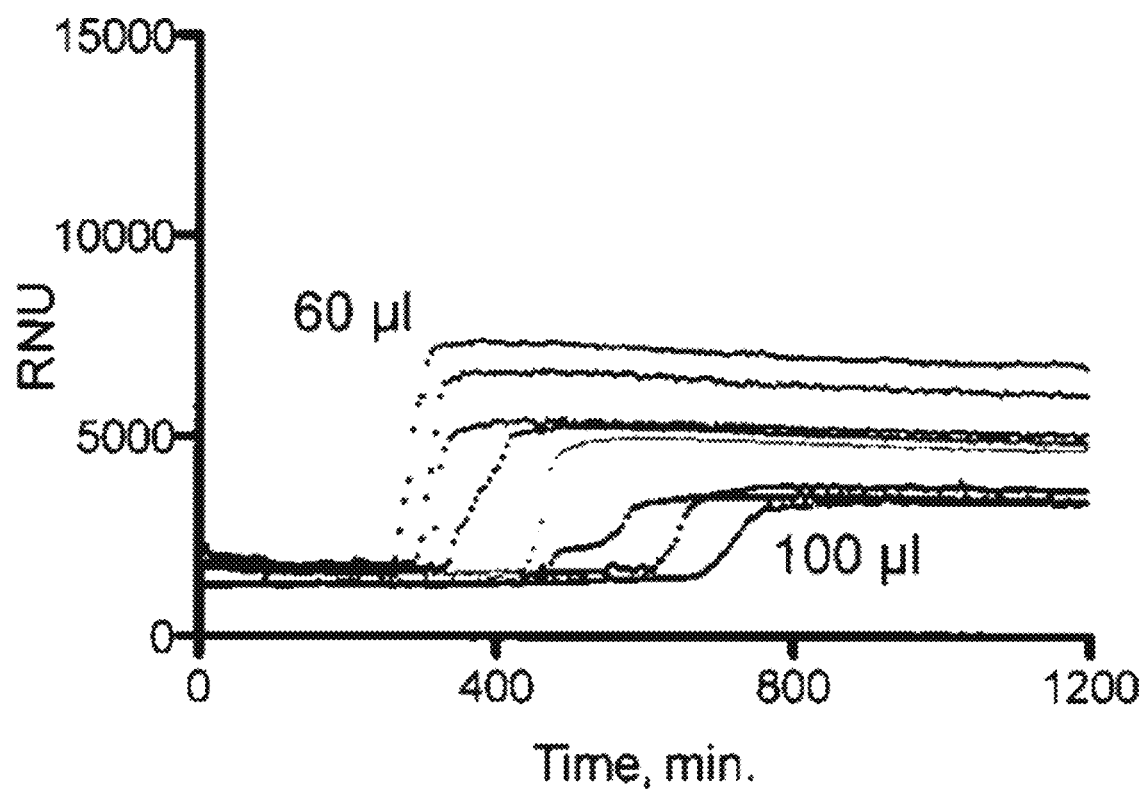
Figure 3A:
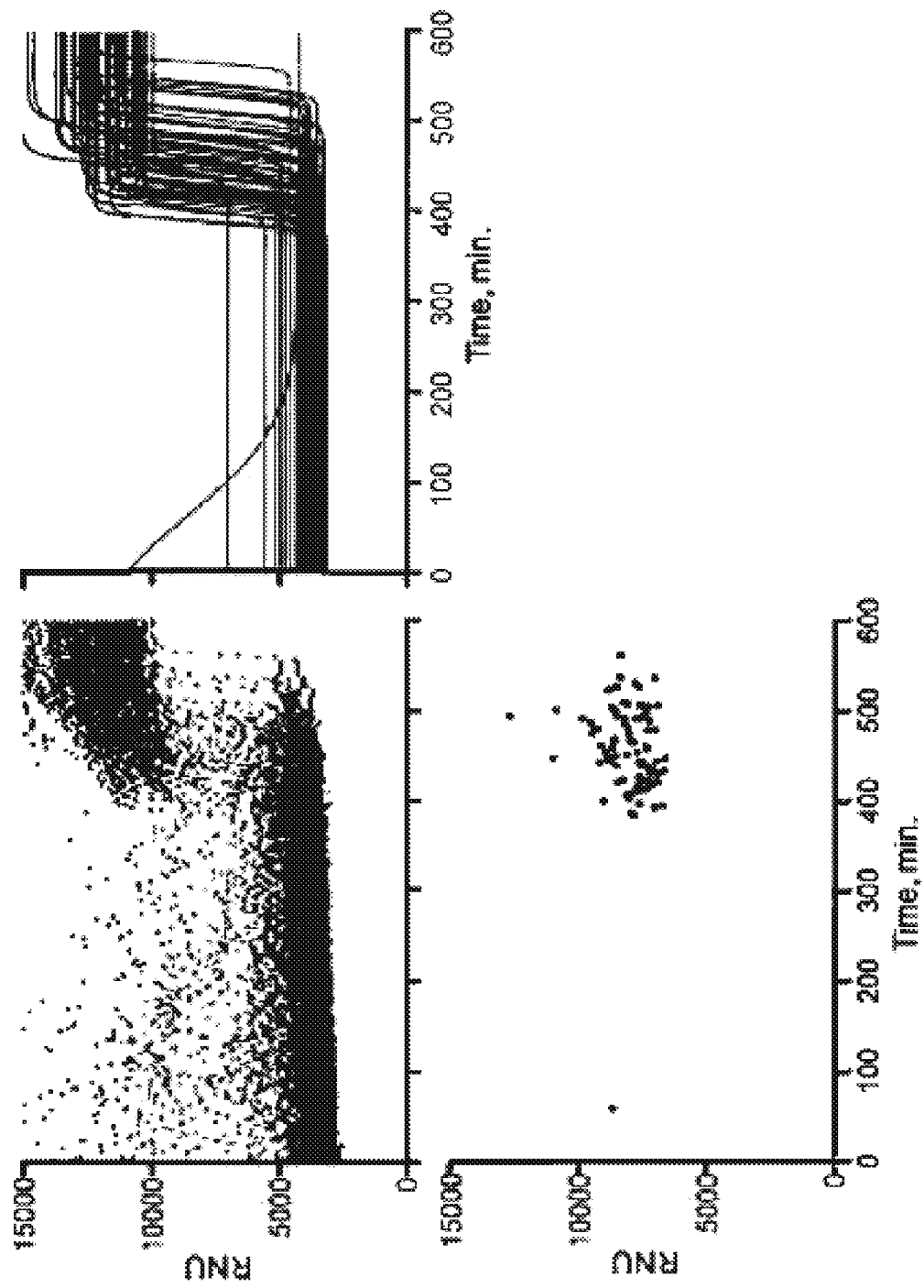
FIG. 3. Nephelometer assay conditions. (A) Assay results when performed with pooled serum from healthy volunteers with the Nephelostar® instrument run at room temperature and the internal radiator set at 37° C. (B) Assay results when performed with pooled serum from healthy volunteers with the Nephelostar® radiator turned off and the assay run in a temperature controlled room set at 34.5° C. The resulting measurement temperature within the Nephelostar® plate holder bay under these conditions was 36.5 to 37° C.

Unfortunately, first attempts to standardize the assay showed an enormous variation even within a given 96-well plate (FIG. 3A), indicating that the transition step is an extremely sensitive physicochemical process, which is sensitive towards subtle variations in pH (FIG. 2C) and serum amounts used (FIG. 2D).

Figure 3B:
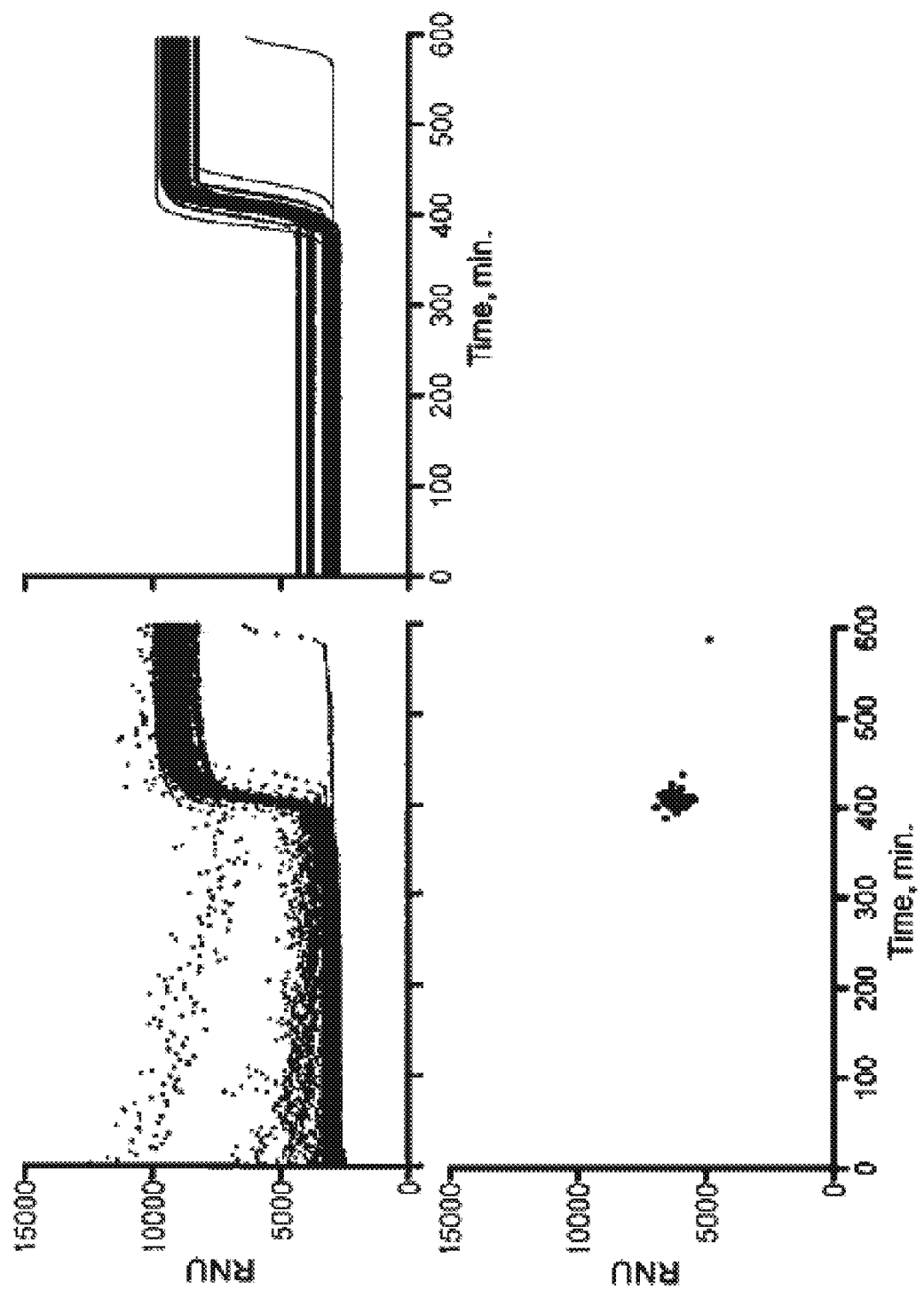

Stabilization of the assay (FIG. 3B) was achieved by introducing three important modifications: (i) assay temperature was stabilized by running the assay in a Special constant temperature room with the intrinsic radiator of the Nephelostar® turned off, (ii) pipetting volumes were stabilized by using a high precision 96-well pipetting device (the Liquidator96™) instead of multi-channel pipettes, and (iii) temperature-sensitivity of the test was diminished by using Hepes instead of the more temperature-sensitive Tris buffer (FIG. 2B). Under these conditions, the assay was stable and yielded highly reproducible results (FIG. 3B) with an intra-day variability of +/−5.2% and an inter-day variability of +/−11.6% in our hands.

Figure 4A:
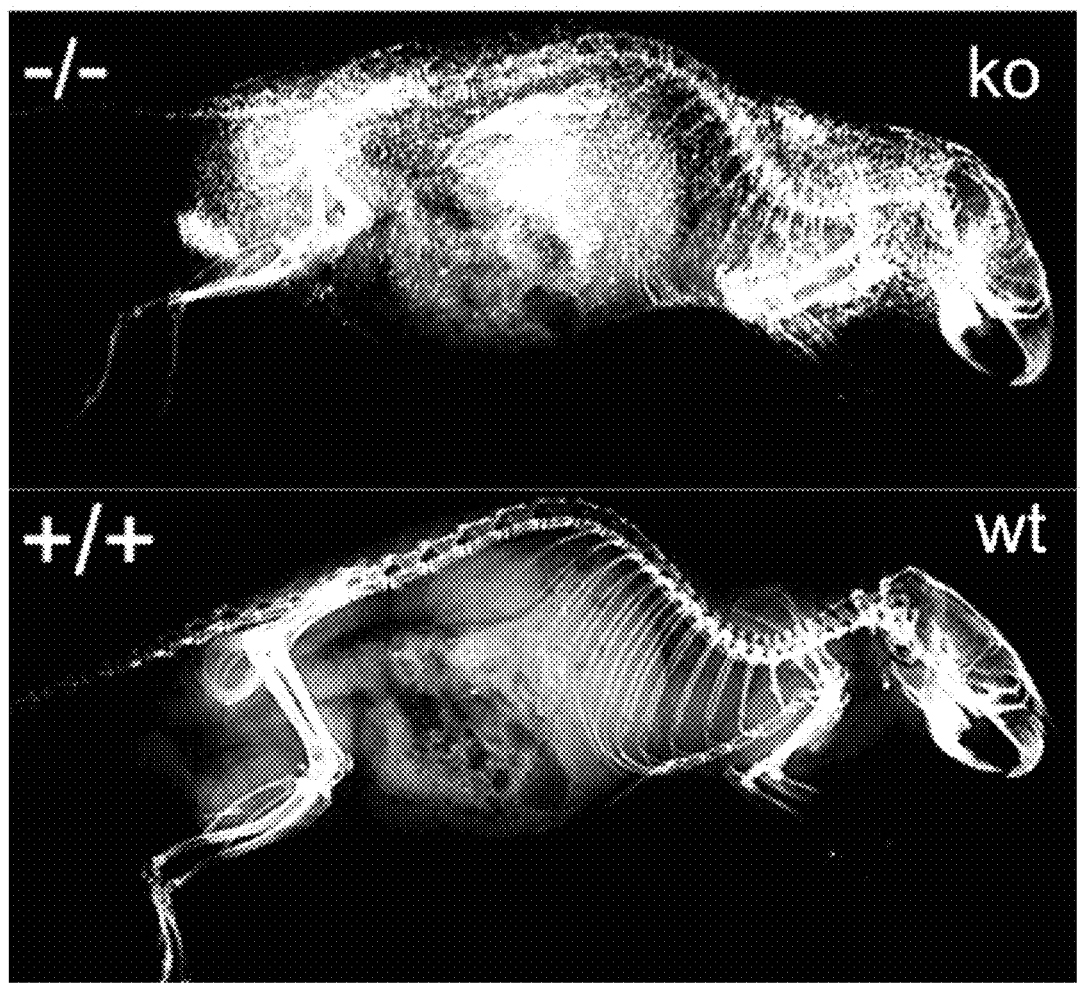
FIG. 4. Nephelometer assay in calcifying animal models. (A) Illustrating representative x-rays of 10 to 16 week old dba2 fetuin-A knock-out (−/−) and wildtype (+/+) mice showing excessive pathological calcifications of fetuin-A knock-out mice. Heterozygous mice have the same phenotype as wildtype mice. (B) Discrimination of wild type (wt), heterozygous (het) and knock out (ko) mouse sera. (C) Results of nephelometer assay performed with serum from fetuin-A knock-out, heterozygous and wildtype mice. (D) Illustrating representative histology of aortas from 16 week old adenine-treated uremic rats with calcifications of the vessel media (Alizarin stain for calcium), and healthy rats without calcifications. (E) Comparison between samples from uremic and non-uremic animals. (F) Nephelometry assay with sera from 20 hemodialysis patients (black) and 20 healthy volunteers (grey).
Figure 4B:
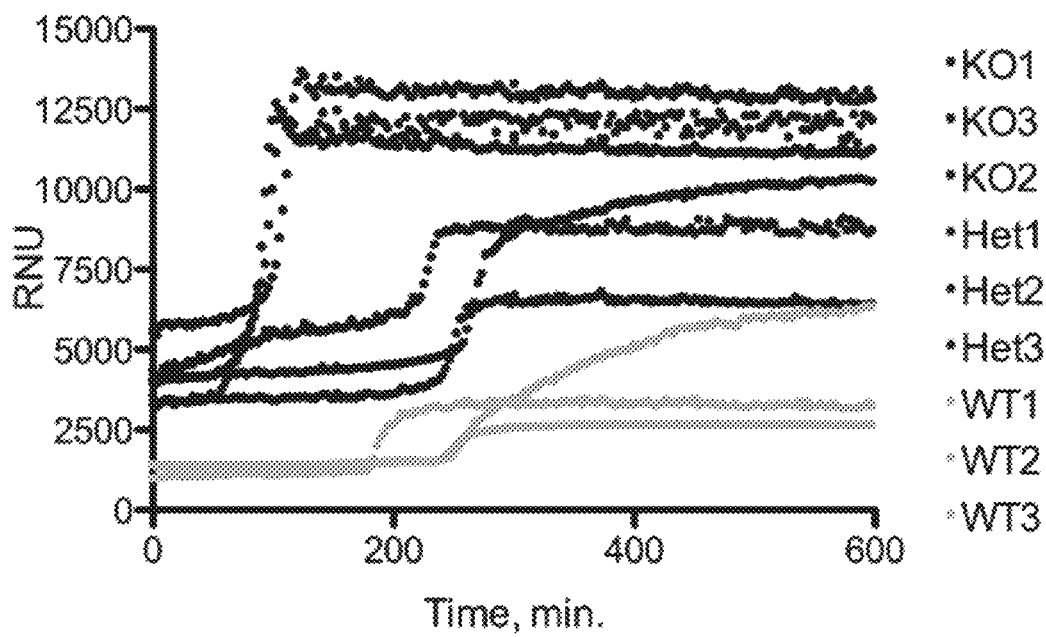
Figure 4C:
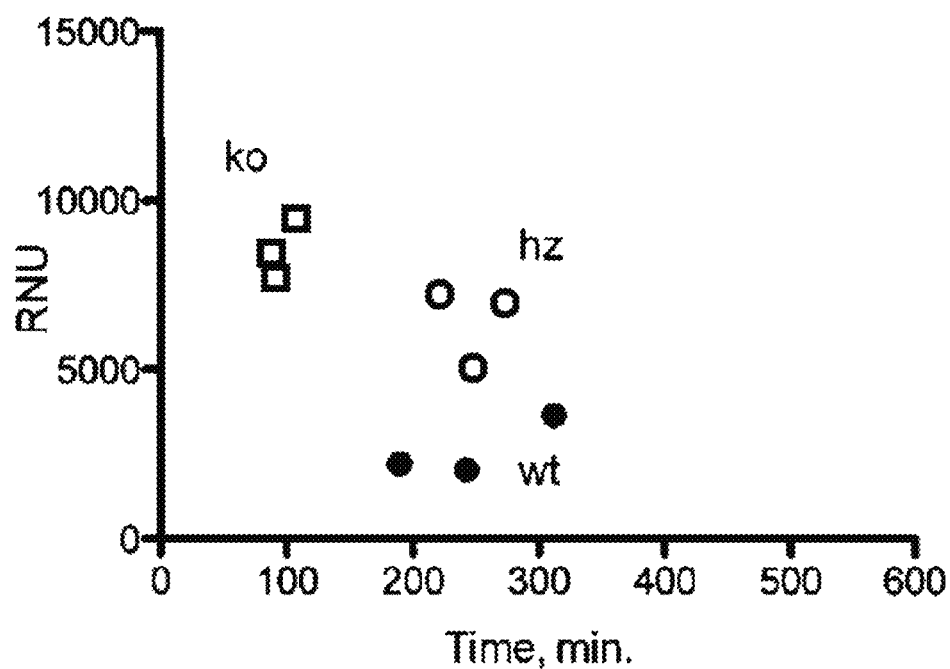
Figure 4D:
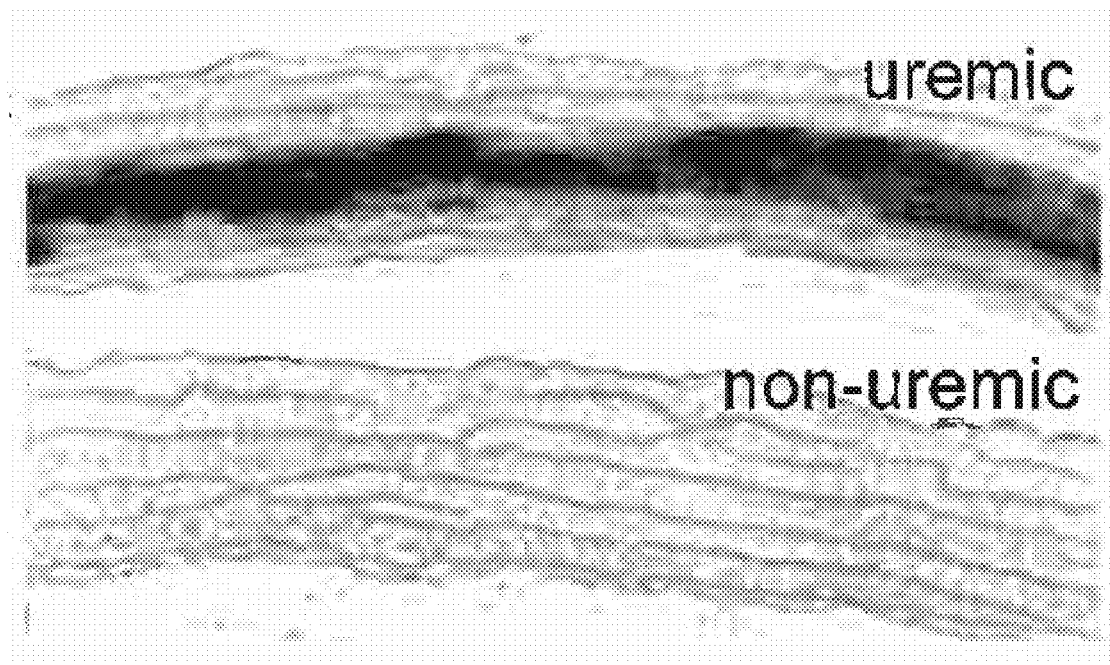
Figure 4E:
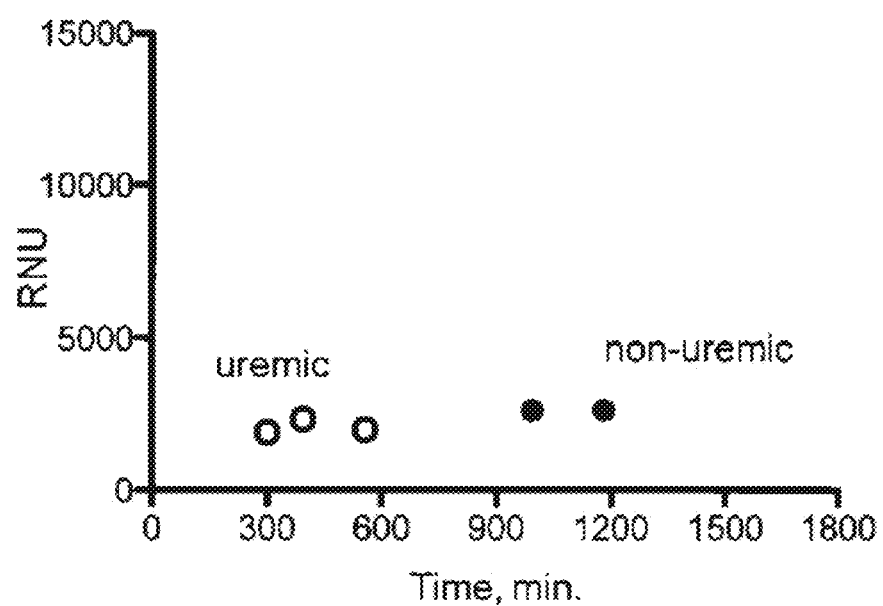

To confirm the correlation between the assay results and calcifications in vivo, we compared serum of fetuin-A knock-out (ko), heterozygous (het) and wildtype (wt) mice (FIGS. 4A, B and C) and found that $T_{50}$ was shorter in serum from the knockout mouse (ko), when compared to heterozygous and wildtype mice. The same pattern was found when serum from calcifying uremic rats and from healthy non-calcifying rats was compared (FIGS. 4D and E). Here again the transition ($T_{50}$) occurred earlier in the calcifying than in the non-calcifying animals.

Figure 4F:
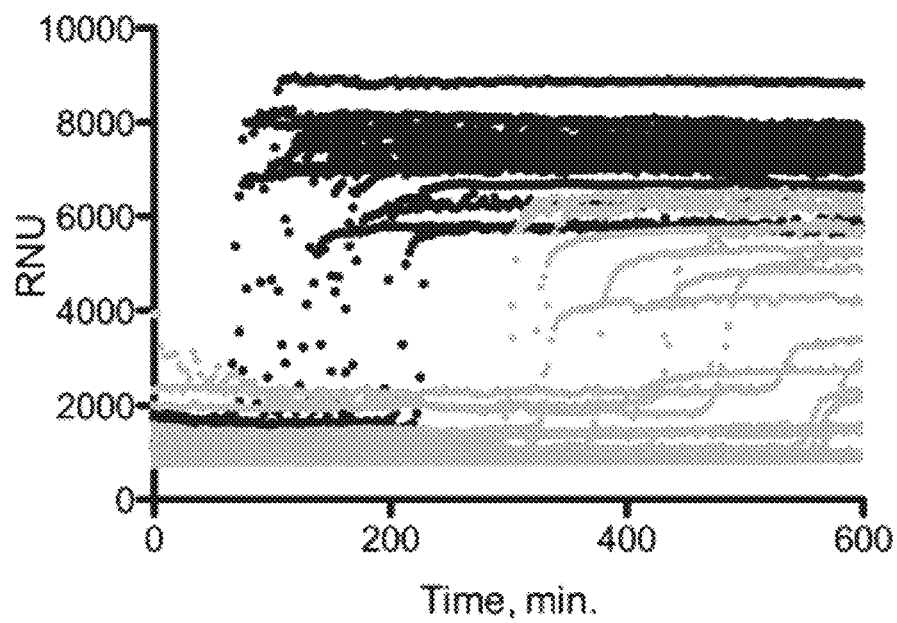
Figure 5A:
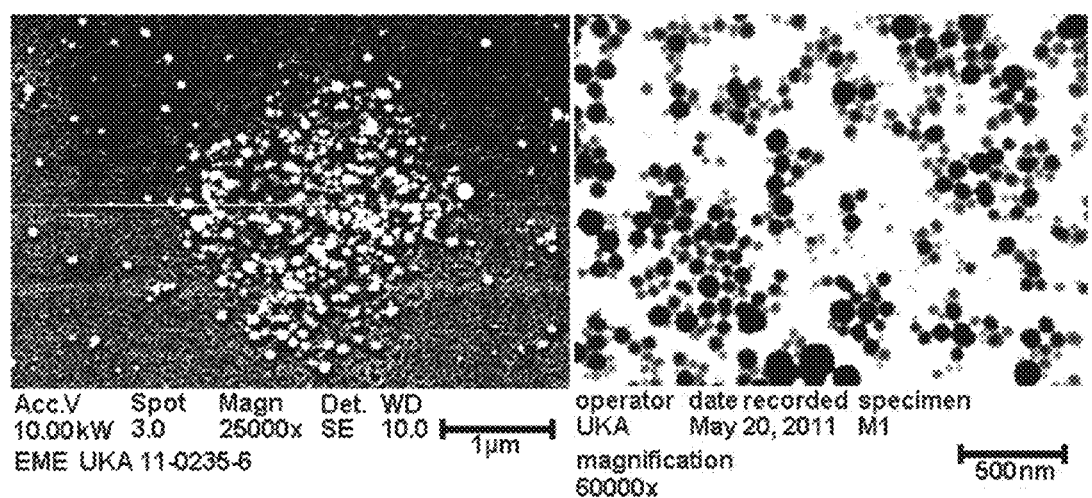
FIG. 5. Particle characterization, microscopic appearance and molecular composition of the CPPs. (A) Scanning electron microscopy (SEM) (left) and transmission electron microscopy (TEM) (right) of primary CPPs. (B) SEM (left) and TEM (right) of secondary CPPs. (C) Coomassie blue stain of protein contents of primary and secondary CPPs (left) and albumin and fetuin-A western blots of primary and secondary CPPs (right). (D) Disappearance of phosphate from the solution upon formation of CPPs.
Figure 5B:
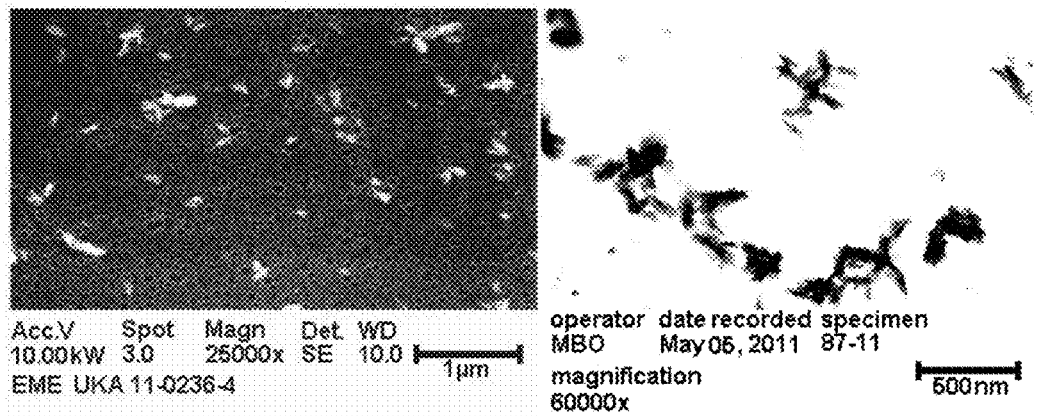
Figure 5C:
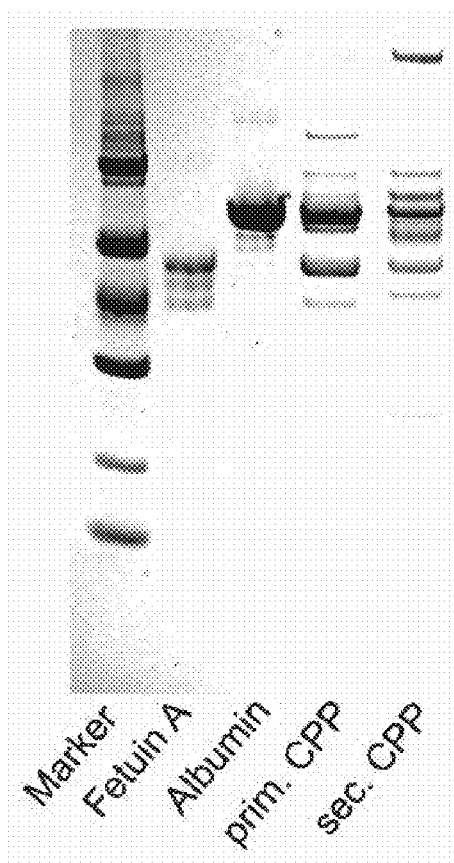
Figure 5C:
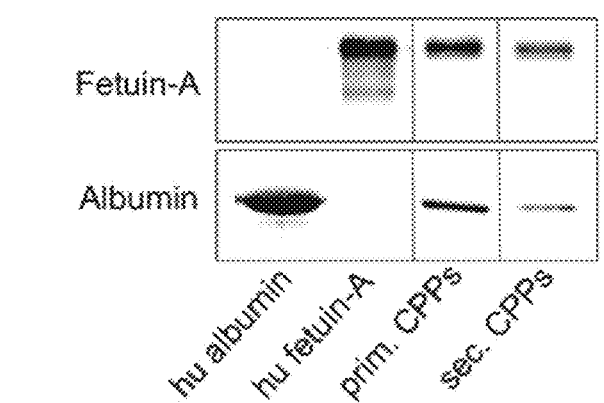
Figure 5D:
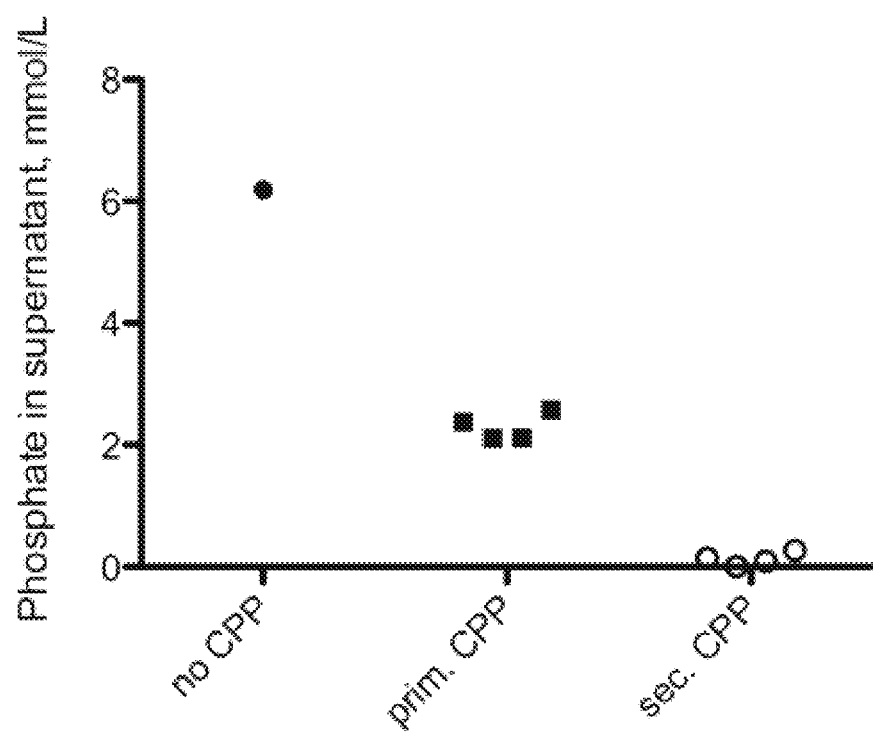
Figure 6A:
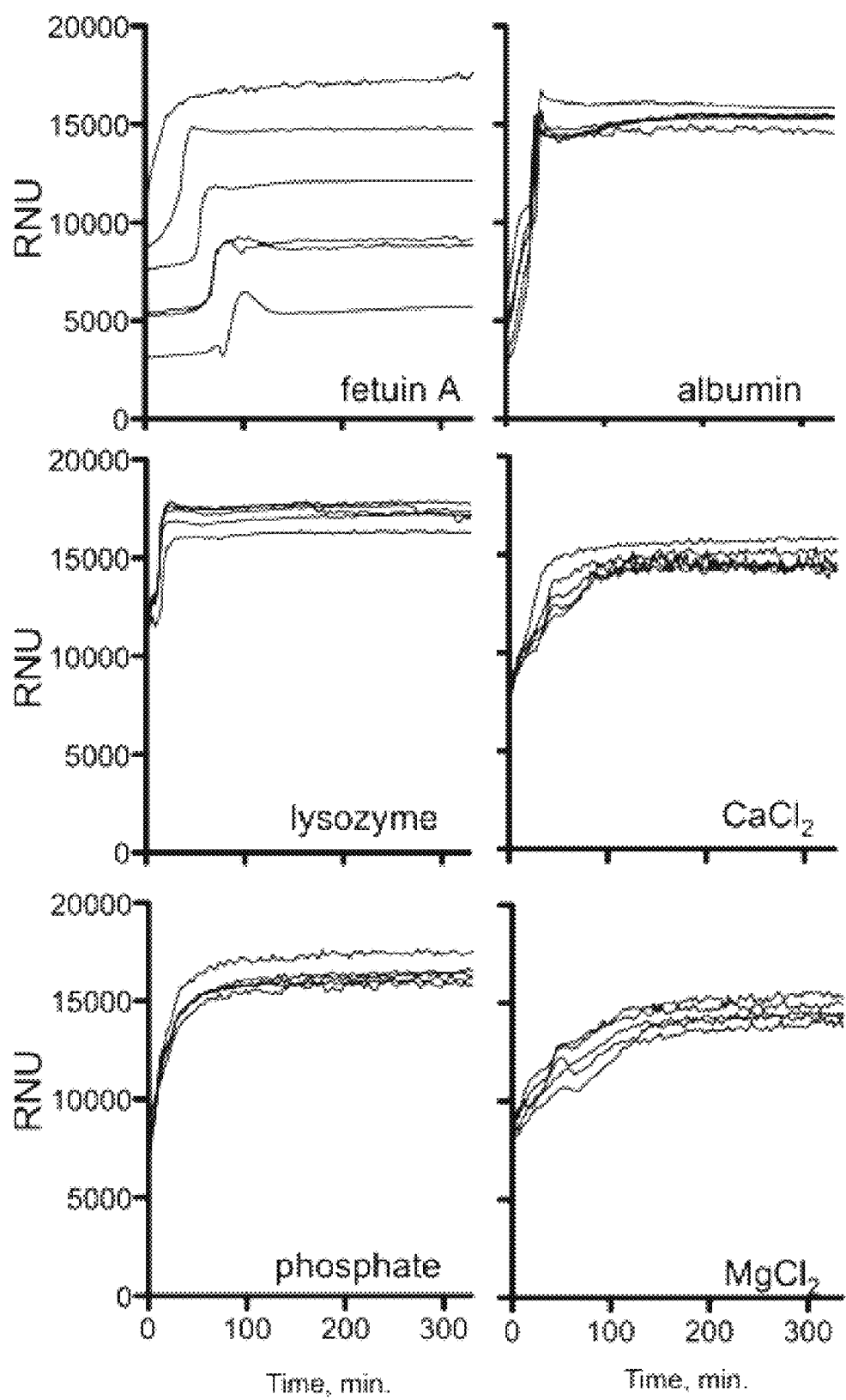
FIG. 6. Assay dependence of spiked serum components. (A) Nephelometry in the absence of serum: only spiking of fetuin A, the strongest intrinsic serum calcification inhibitor significantly influences the assay. (B) Nephelometry in the presence of serum: all spiked substances influence the assay. (C) Alternative presentation of the data shown in B. Substance concentrations used in (a) and (B) were the same as given in the legend of (C).
Figure 6B:
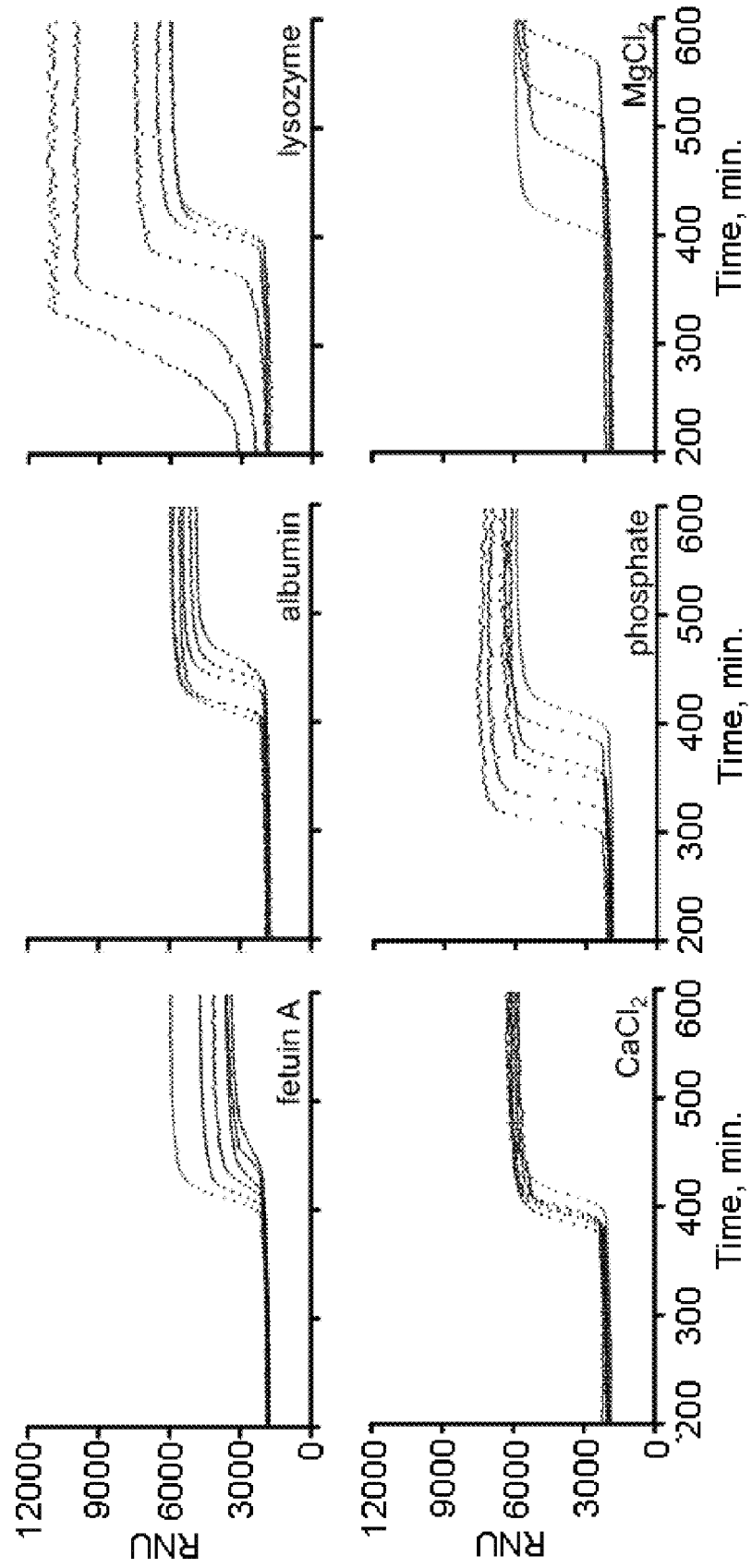
Figure 6C:
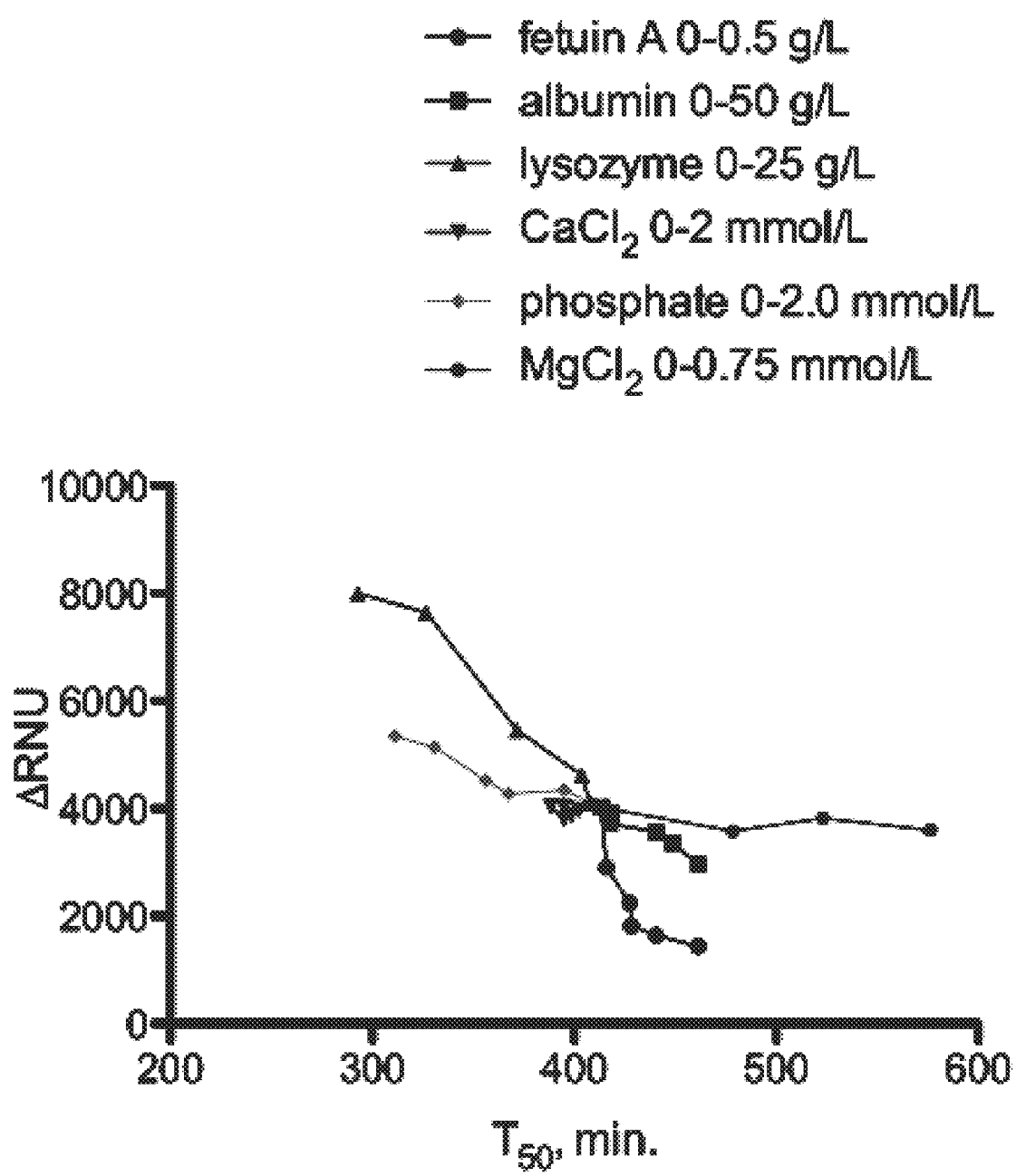
Figure 7A:
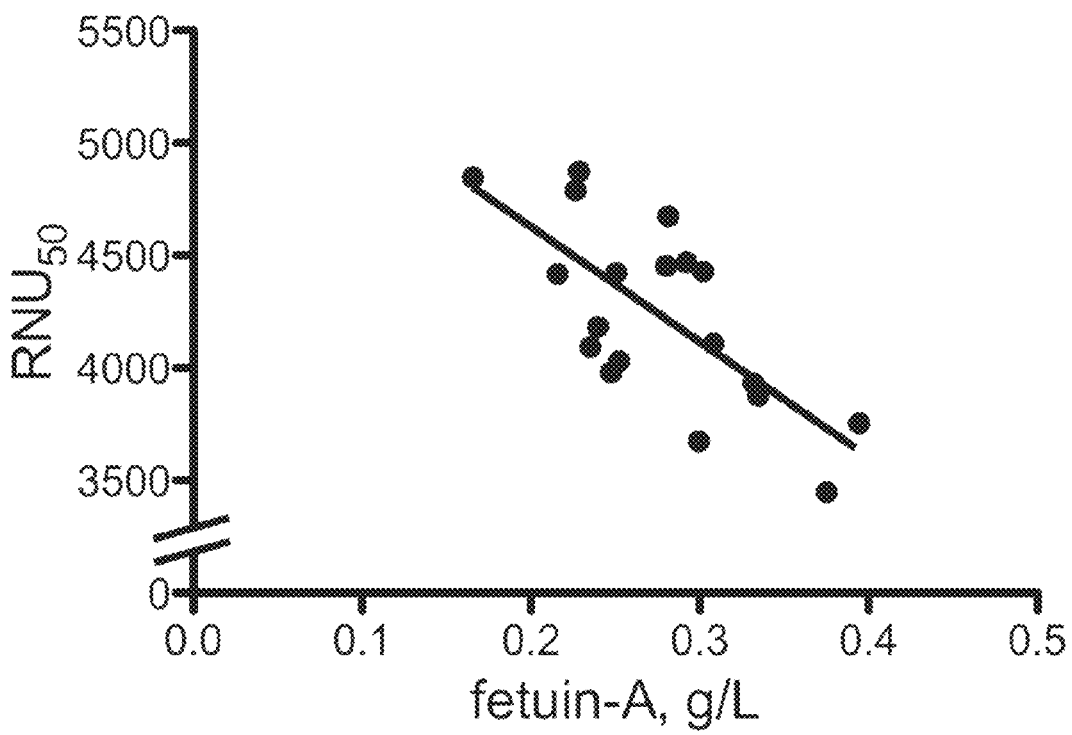
FIG. 7. Correlation of one-halfmaximal relative nephelometric units ($RNU_{50}$) and $T_{50}$ with fetuin-A serum concentrations. Fetuin-A concentrations were measured in sera obtained from 20 hemodialysis patients and plotted against the $RNU_{50}$ and $T_{50}$ values obtained from the assay of the present invention. Fetuin-A concentrations highly correlated with (A) $RNU_{50}$ (p=0.0006) and (B) $T_{50}$ (p=0.0413). Patient sera were the same as used for the experiment shown in FIG. 4F. Fetuin-A serum concentrations were measured by ELISA as described by Ketteler M, et al. (Kettler et al., 2003).
Figure 7B:
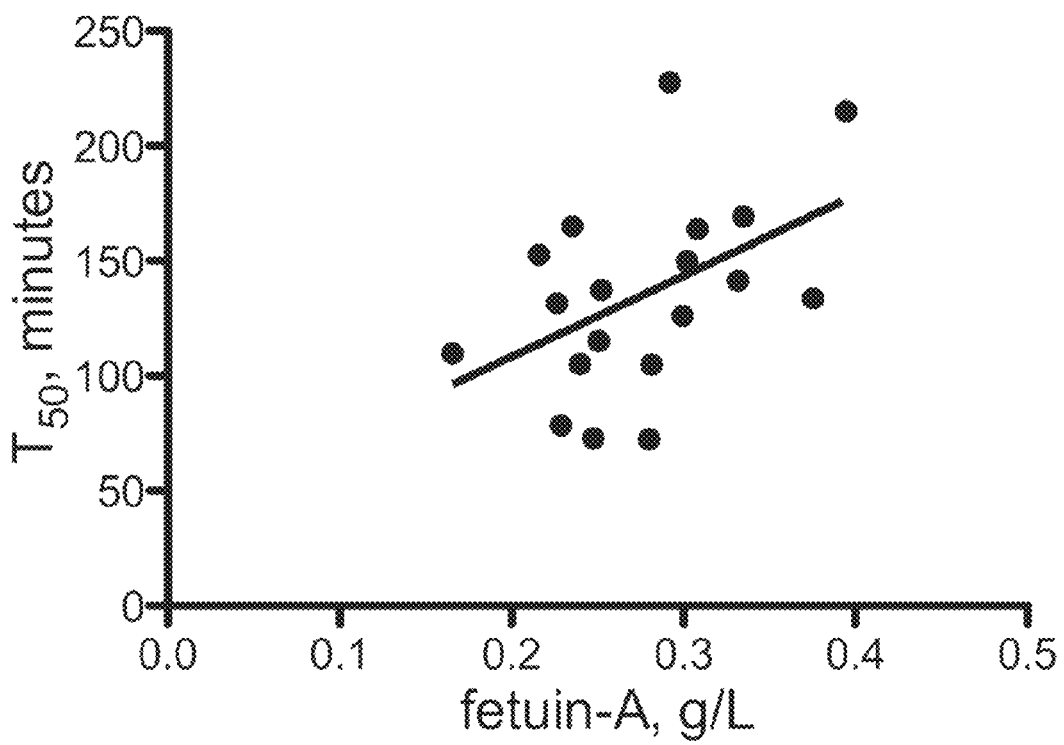

We also tested sera from healthy volunteers and hemodialysis patients. Again, the test discriminated the calcification-prone from the noncalcificationprone individuals (i.e., the hemodialysis patients from the healthy volunteers (FIG. 4F), indicating that the test reflects calcification propensity in serum.

These results confirm that the nephelometer assay presented here provides an estimate of intrinsic serum-related calcification propensity.

The test of the present invention increases supersaturation of serum by adding Ca (10 mM) and phosphate (6 mM). The specific effect of supersaturation depends on the intrinsic concentrations of fetuin-A, albumin, phosphate etc. in a given serum. As a general rule, the higher the calcium and phosphate supersaturation, the lower $T_{50}$ and the higher $RNU_{50}$. This applies to sera from HD patients and healthy volunteers alike. $RNU_{50}$ largely depends on the protein content (fetuin-A, albumin) of the CPPs with some contribution of phosphate. $T_{50}$ largely depends on Mg and phosphate with some contribution of fetuin-A and albumin. A low $T_{50}$ is therefore often associated with a high $RNU_{50}$ and vice versa. A universal $RNU_{50}$-to-$T_{50}$-ratio can however, not be determined as both variables depend on different—albeit overlapping—determinants.

In summary, we present a nephelometer-based assay, which measures calcification propensity of a body fluid, exemplarily shown in blood serum. Given the wide area of potential applications of this assay, this method is a useful tool for the investigation and elucidation of biomineralization-related issues in clinical as well as scientific research and in diagnosis in vivo and ex vivo.

REFERENCES

1. Heiss, A. et al. (2003), Structural basis of calcification inhibition by alpha 2-HS glycoprotein/fetuin-A. Formation of colloidal CPPs, *J Biol Chem* 278, 13333-13341.
2. Heiss, A. et al. (2008), Hierarchical role of fetuin-A and acidic serum proteins in the formation and stabilization of calcium phosphate particles, *J Biol Chem* 283, 14815-14825.
3. Jahnen-Dechent, W. et al. (1997), Cloning and targeted deletion of the mouse fetuin gene, *J Biol Chem* 272, 31496-31503.
4. Jahnen-Dechent, W., Sch äfer, C, Heiss, A. and Grotzinger, J. (2001), Systemic inhibition of spontaneous calcification by the serum protein alpha 2-HS glycoprotein/fetuin, *Z Kardiol* 90 Suppl 3, 47-5.
5. Jahnen-Dechent, W., Heiss, A., Sch äfer, C., Kettler, M. (2011), Fetuin-A Regulation of Calcified Matrix Metabolism, *Circulation Research* 108, 1494-1509.
6. Ketteler M, Bongartz P, Westenfeld R, Wildberger J E, Mahnken A H, B öhm R, Metzger T, Wanner C, Jahnen-Dechent W, Floege J (2003), Association of low fetuin-A (AHSG) concentrations in serum with cardiovascular mortality in patients on dialysis: a cross-sectional study, *Lancet* 361: 827-833.
7. Pasch, A. et al. (2008), Sodium thiosulfate prevents vascular calcifications in uremic rats, *Kidney Int* 74, 1444-1453.
8. Reynolds, J. L., et al. (2005), Multifunctional roles for serum protein fetuin-a in Inhibition of human vascular smooth muscle cell calcification, *J Am Soc Nephrol* 16, 2920-2930
9. Reynolds, J. L., et al. (2004), Human vascular smooth muscle cells undergo vesicle-mediated calcification in response to changes in extracellular calcium and phosphate concentrations: a potential mechanism for accelerated vascular calcification in ESRD, *J Am Soc Nephrol* 15, 2857-2867.
10. Sch äfer, C. et al. (2003), The serum protein alpha 2-Heremans-Schmid glycoprotein/fetuin-A is a systemically acting inhibitor of ectopic calcification, *J Clin Invest* 112, 357-366.
11. Wald, J., et al. (2011), Formation and stability kinetics of calcium phosphate-fetuin-A colloidal particles probed by time-resolved dynamic light scattering, *Soft Matter.*
12. Wu, C. Y., Martel, J., Young, D. and Young, J. D. (2009), Fetuin-A/albumin-mineral complexes resembling serum calcium granules and putative nanobacteria: demonstration of a dual inhibition-seeding concept, *PLoS One* 4, e8058.

13. Young, J. D., et al. (2009), Putative nanobacteria represent physiological remnants and culture by-products of normal calcium homeostasis, *PLoS One* 4, e4417.
14. Young, J. D., et al. (2009), Characterization of granulations of calcium and apatite in serum as pleomorphic mineralo-protein complexes and as precursors of putative nanobacteria. *PLoS One* 4, e5421.
15. Yusuf, S., Reddy, S., Ounpuu, S, and Anand, S. (2001), Global burden of cardiovascular diseases: part I: general considerations, the epidemiologic transition, risk factors, and impact of urbanization, *Circulation* 104, 2746-2753.

The invention claimed is:

1. A method for determining the propensity of a body fluid obtained from an individual for calcification comprising:
   (i) adding a soluble calcium salt and a soluble phosphate salt to a sample of said body fluid;
   (ii) incubating said sample at conditions allowing the formation of calciprotein particles (CPPs); and
   (iii) determining one or more of the following:
      (a) a rate of the formation of primary and/or secondary CPPs;
      (b) an amount of primary and/or secondary CPPs; and/or
      (c) a rate of transition of primary CPPs into secondary CPPs,
   wherein an increase over what is determinable for a fluid with known calcification in one or more of (a), (b) and/or (c) of step (iii) indicates an increased propensity of said body fluid for calcification.

2. The method of claim 1, wherein step (iii) is performed by an optical method.

3. The method of claim 2, wherein excitation light used in the optical method is a laser beam.

4. The method of claim 2, wherein the optical method is performed by detecting light scattering.

5. The method of claim 4, wherein the method of detecting light scattering is selected from the group consisting of: dynamic light scattering, cross-correlation dynamic light scattering, three-dimensional cross-correlation dynamic light scattering, or nephelometry.

6. The method of claim 2, wherein the optical method is a method selected from the group consisting of:
   absorptiometry,
   detection of light scattering,
   correlation spectroscopy,
   or a combination of two or more thereof.

7. The method of claim 1, wherein step (iii) is performed by any method selected from the group consisting of:
   sedimentation techniques,
   filtration analysis,
   size exclusion chromatography,
   granulometry,
   acoustic spectroscopy,
   or a combination of two or more thereof.

8. The method of claim 1, wherein the fluid is a body fluid obtained from a patient that has developed calcification and/or is at risk of developing calcification.

9. The method of claim 8, wherein the patient suffers from vascular, valvular and/or soft tissue calcification.

10. The method of claim 9, wherein said patient further suffers from a rheumatoid disease, a malignant disease and/or an infectious disease, or wherein the patient shows at least one of the syndromes selected from the group consisting of:
    renal dysfunction,
    hypertension,
    diabetes mellitus,
    dyslipidemia,
    a lack of adequate mineralization, and
    atherosclerosis.

11. The method of claim 10, wherein the lack of adequate mineralization is due to osteoporosis, osteomalacia, or a combination thereof.

12. The method of claim 8, wherein said patient is a dialysis patient.

13. The method of claim 1, wherein said method is performed at a constant temperature and/or at a constant pH.

14. The method of claim 1, wherein said method is performed in one of the following:
    (a) a multiwell format;
    (b) a flow-through cell; or
    (c) a microfluidic device.

15. The method of claim 1, wherein at least step (iii) is automated, or wherein at least steps (ii) and (iii) are automated, or wherein all of the steps (i), (ii) and (iii) are automated.

16. The method of claim 1, wherein the primary CPPs have an average diameter smaller than 100 nm and the secondary CPPs have an average diameter of larger than 100 nm.

17. The method of claim 1, wherein one or more of (a), (b) and/or (c) of step (iii) is/are compared with one or more control sample(s).

18. The method of claim 1, wherein (c) of step (iii) is determined by determining a time point of half maximal transition time ($T_{50}$) of the transition of primary CPPs into secondary CPPs.

19. The method of claim 1, wherein the body fluid is blood, blood plasma, blood serum, lymph, or urine.

* * * * *